(12) United States Patent
Suzuki et al.

(10) Patent No.: US 9,968,495 B2
(45) Date of Patent: May 15, 2018

(54) ABSORBENT ARTICLE PROVIDED WITH A BODILY FLUID RECEPTION CANAL

(71) Applicant: DAIO PAPER CORPORATION, Shikokuchuo-shi, Ehime (JP)

(72) Inventors: Migaku Suzuki, Chigasaki (JP); Yoshio Hirai, Tokyo (JP)

(73) Assignee: DAIO PAPER CORPORATION, Shikokuchuo-Shi (JP)

( * ) Notice: Subject to any disclaimer, the term of this patent is extended or adjusted under 35 U.S.C. 154(b) by 0 days. days.

(21) Appl. No.: 14/430,509

(22) PCT Filed: Oct. 12, 2012

(86) PCT No.: PCT/JP2012/076389
§ 371 (c)(1),
(2) Date: Mar. 23, 2015

(87) PCT Pub. No.: WO2014/057571
PCT Pub. Date: Apr. 17, 2014

(65) Prior Publication Data
US 2015/0196433 A1     Jul. 16, 2015

(51) Int. Cl.
*A61F 13/15* (2006.01)
*A61F 13/20* (2006.01)
(Continued)

(52) U.S. Cl.
CPC .... *A61F 13/49413* (2013.01); *A61F 13/5123* (2013.01)

(58) Field of Classification Search
CPC ...... A61F 2013/49493; A61F 13/49413; A61F 13/4942
See application file for complete search history.

(56) References Cited

U.S. PATENT DOCUMENTS 4,646,362 A * 3/1987 Heran ............... A61F 13/49009
2/400
6,458,111 B1 * 10/2002 Onishi .................. A61F 13/495
604/369
(Continued)

FOREIGN PATENT DOCUMENTS

EP     2886091 A1    6/2015
GB     2242821      * 10/1991 ............. A61F 13/15
(Continued)

OTHER PUBLICATIONS

"Notch." Merriam-Webster.com. Merriam-Webster, n. d. Web. Sep. 27, 2017.*
(Continued)

*Primary Examiner* — Michele M Kidwell
(74) *Attorney, Agent, or Firm* — Oliff PLC

(57) ABSTRACT

An absorbent including: an absorbent body (AB) having a leak preventer sheet form and absorber for absorbing fluid, minimum one layer arranged above the leak preventer; a connection structure arranged from the AB's front to rear end parts in direction via front, crotch part and rear, the connection structure coupling to the AB at front and rear end parts; the connection structure has right and left belt-like supporters and connection sheet (CS), right and left edge parts of the CS respectively coupling to right and left belt-like supporters, the CS hangs down, on the belt-like supporters underside, toward the absorber in front, crotch part and rear, to form a canal with right and left edge parts vicinities of the CS serving as side surfaces and vicinity of the CS center part in lateral direction serving as bottom surface, the fluid canal enables the fluid from a wearer to the absorber.

19 Claims, 28 Drawing Sheets

(51) Int. Cl.
*A61F 13/494* (2006.01)
*A61F 13/512* (2006.01)

(56) References Cited

U.S. PATENT DOCUMENTS

| | | | |
|---|---|---|---|
| 7,166,095 B1 * | 1/2007 | Coates | A61F 13/505 |
| | | | 604/385.14 |
| 8,795,249 B2 * | 8/2014 | Minato | A61F 13/4942 |
| | | | 604/385.19 |
| 2004/0039363 A1 | 2/2004 | Sugiyama et al. | |
| 2015/0190289 A1 | 7/2015 | Suzuki et al. | |
| 2015/0230997 A1 * | 8/2015 | Suzuki | A61F 13/4942 |
| | | | 604/385.28 |

FOREIGN PATENT DOCUMENTS

| | | |
|---|---|---|
| JP | H03-231664 A | 10/1991 |
| JP | H11-244331 A | 9/1999 |
| JP | 2000-083999 A | 3/2000 |
| JP | 2002-143217 A | 5/2002 |
| JP | 2002-204811 A | 7/2002 |
| WO | 95/32699 * | 7/1995 ............. A61F 13/15 |
| WO | 2008-138018 A1 | 11/2008 |
| WO | 2014-030200 A1 | 2/2014 |

OTHER PUBLICATIONS

"Pore." Merriam-Webster.com. Merriam-Webster, n. d. Web. Sep. 27, 2017.*
Nov. 6, 2012 Written Opinion issued in International Patent Application No. PCT/JP2012/076389.
Dec. 11, 2012 Office Action issued in Japanese Patent Application No. 2012-547346.
Nov. 6, 2012 International Search Report issued in International Patent Application No. PCT/JP2012/076389.
Apr. 22, 2016 Extended European Search Report issued in Application No. 12886315.6.

* cited by examiner

FIG. 2
(A)
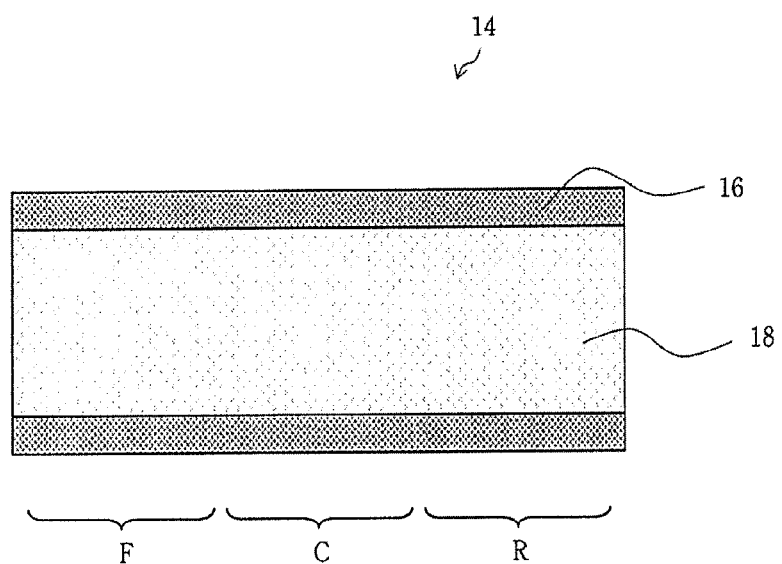
(B)
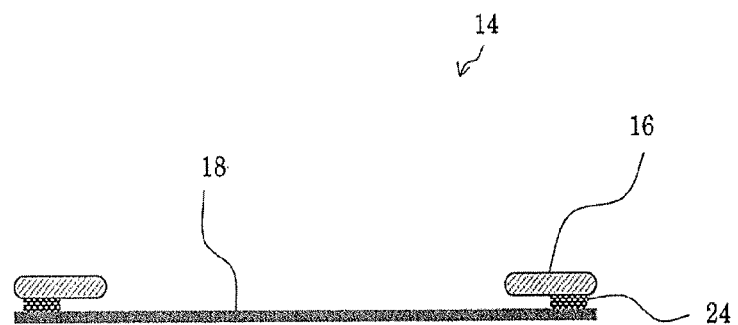

FIG. 4
(A)
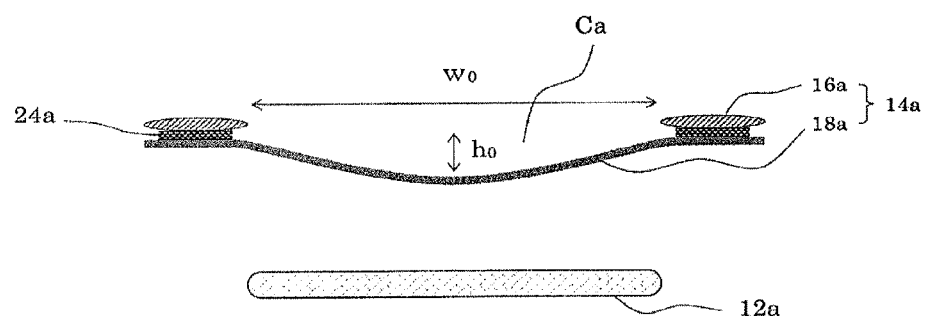
(B)
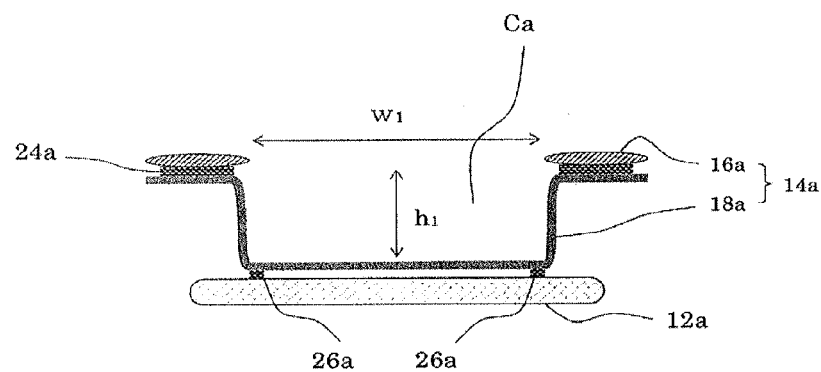
(C)
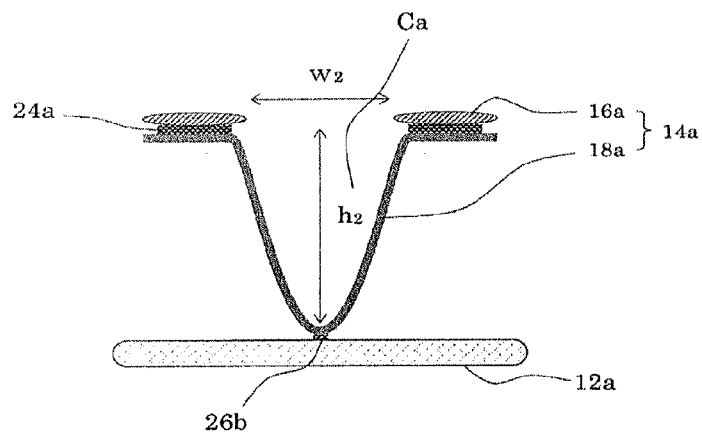

FIG. 5
(A)　　　　(B)　　　　(C)　　　　(D)
   
(E)　　　　　(F)　　　　　(G)
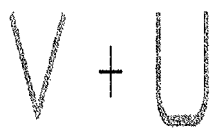 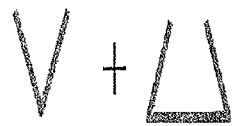 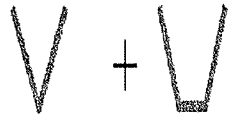
(H)　　　　　(I)　　　　　(J)
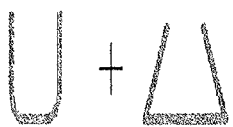 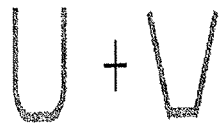 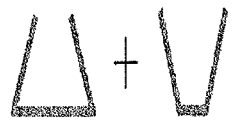

FIG. 7
(A)
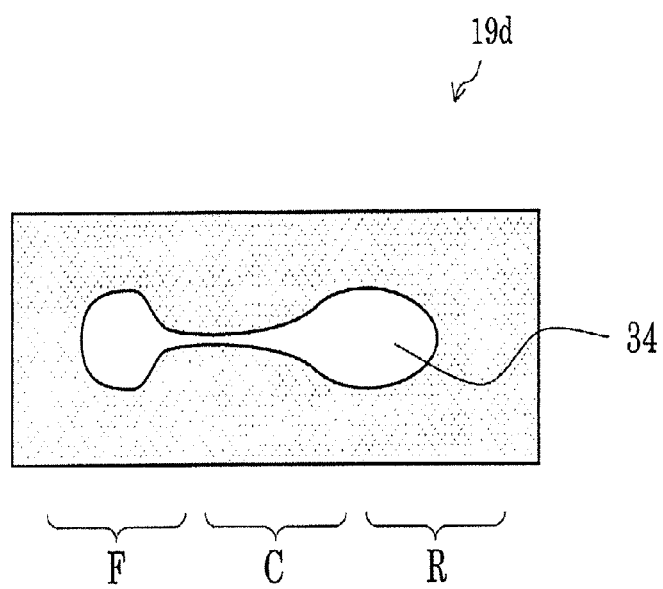
(B)
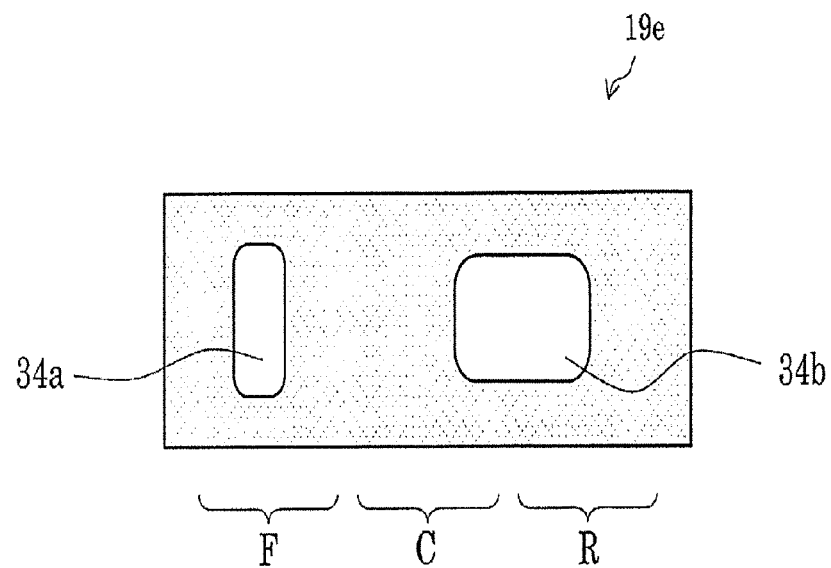

FIG. 8
(A)
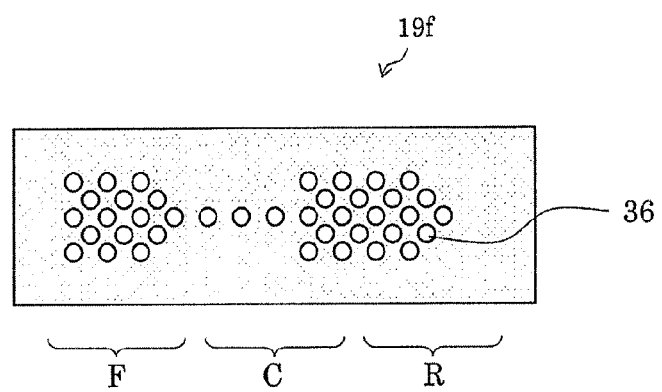
(B)
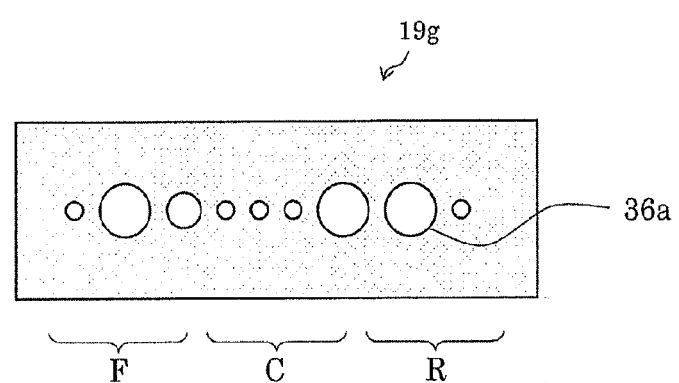
(C)
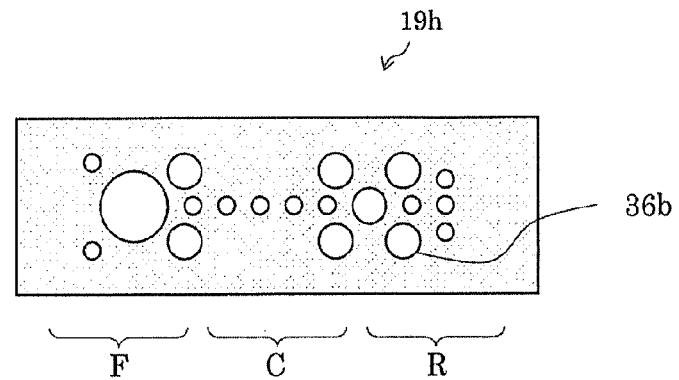

FIG. 9
(A)
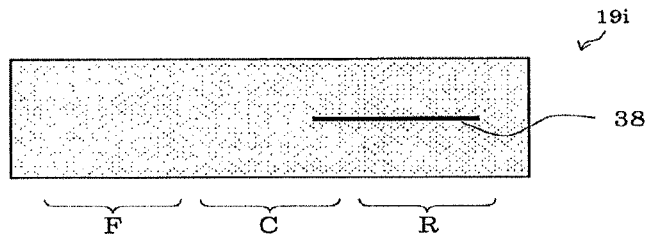
(B)
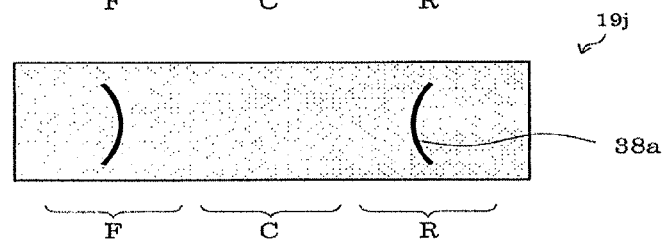
(C)
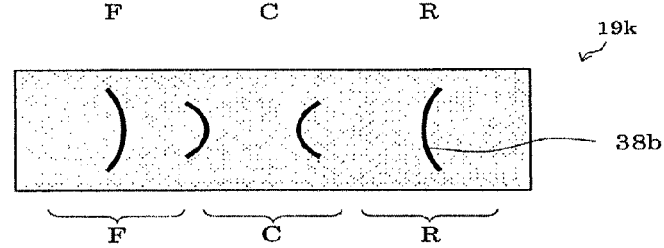
(D)
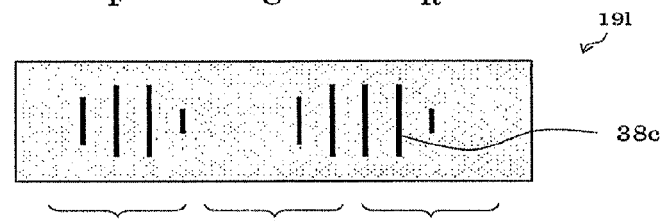
(E)
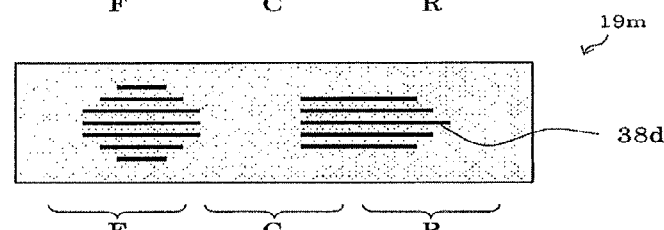
(F)
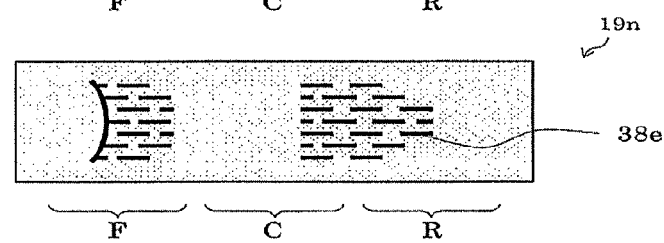

FIG. 10
(A)
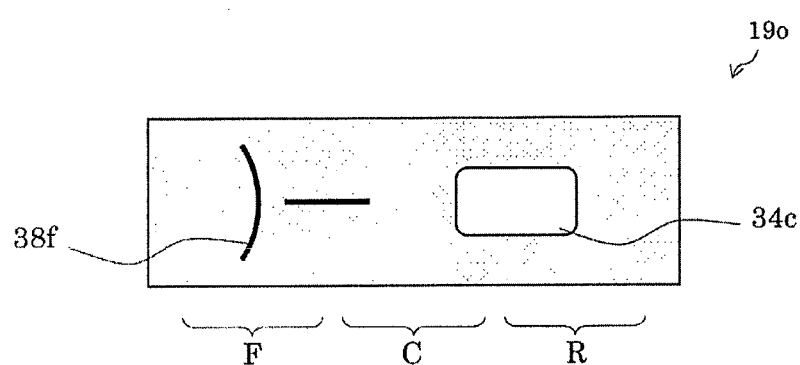
(B)
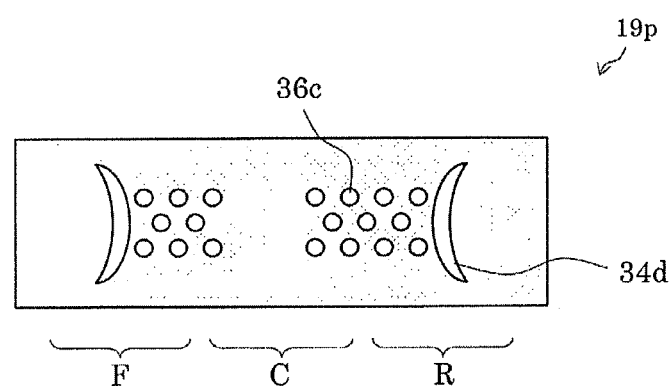

FIG. 14
(A)
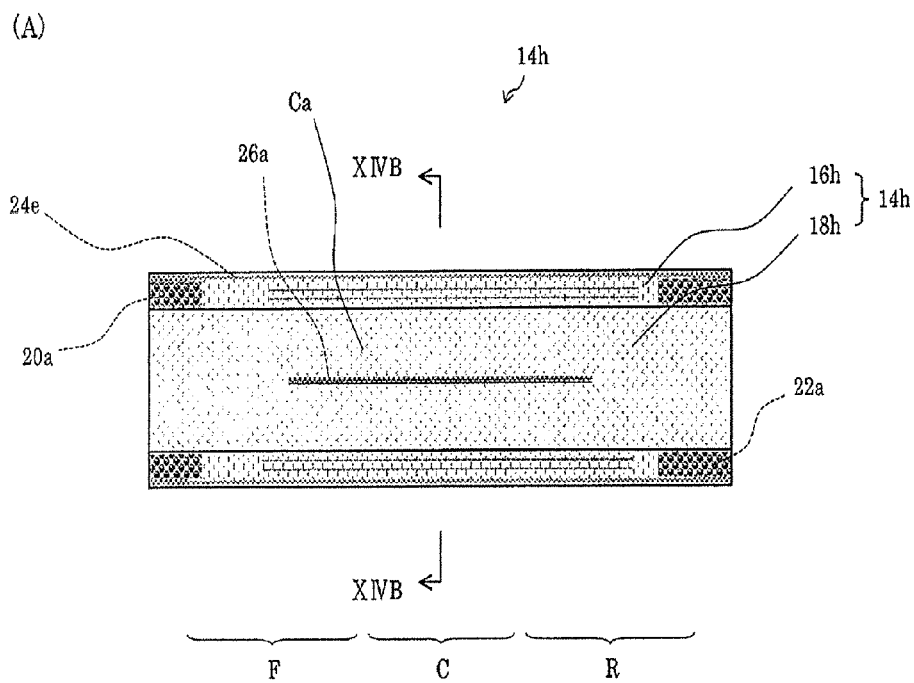
(B)
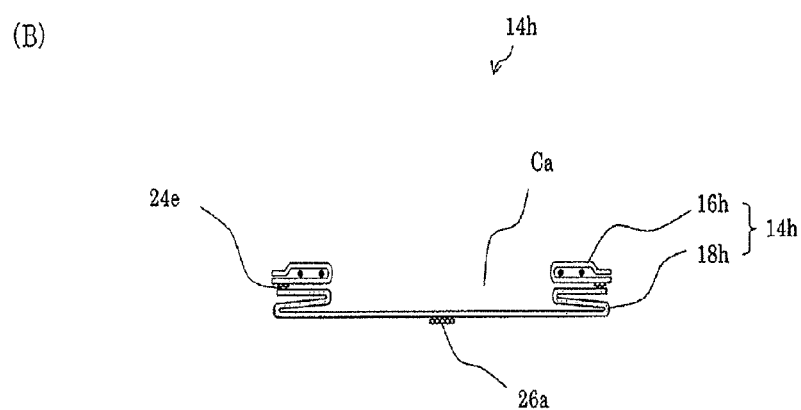

FIG. 17
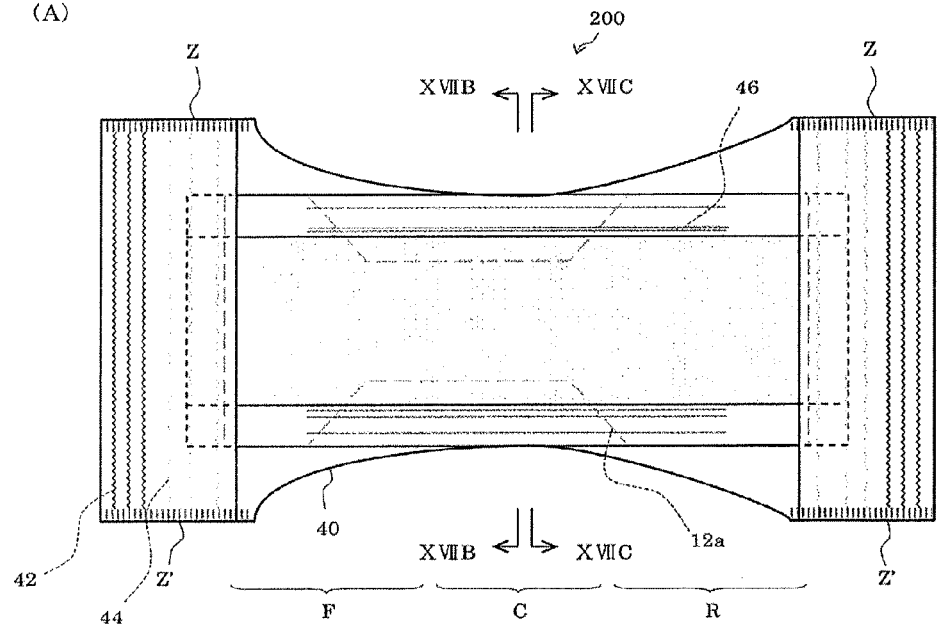
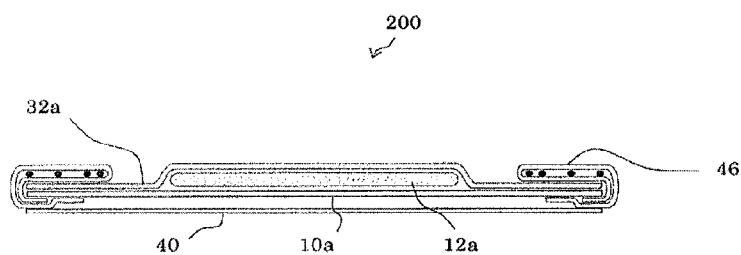
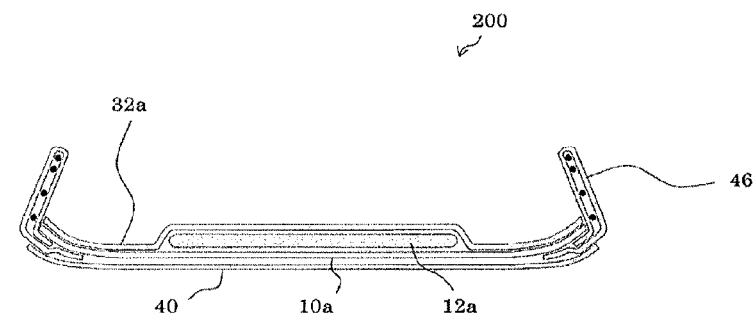

FIG. 18
(A)
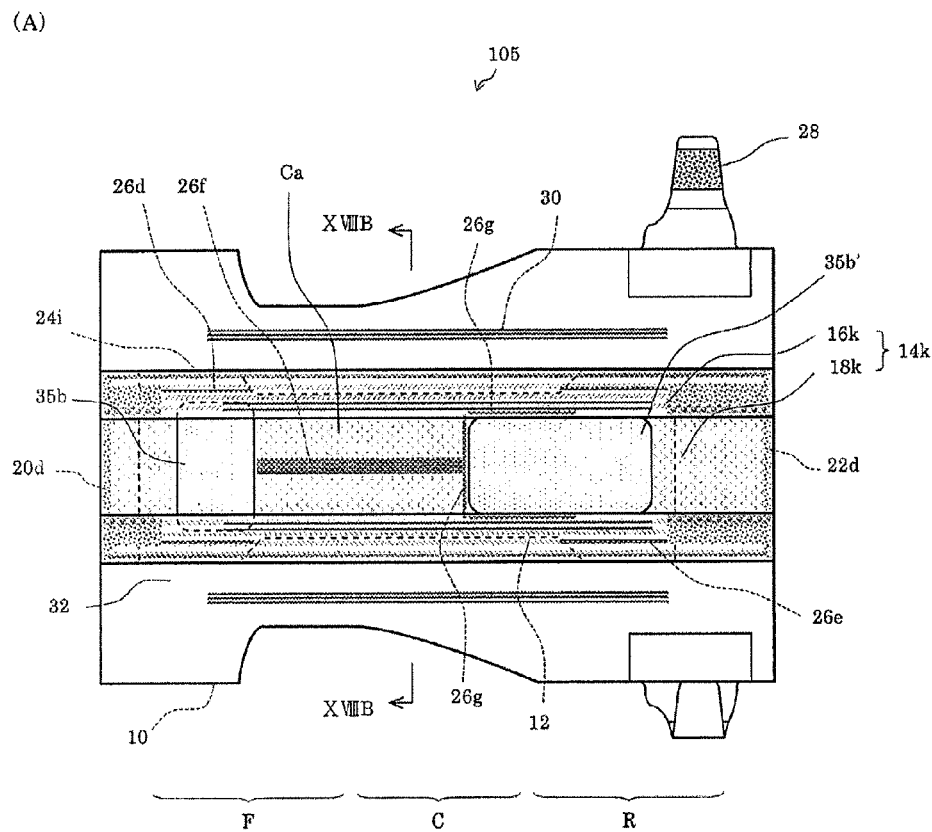
(B)
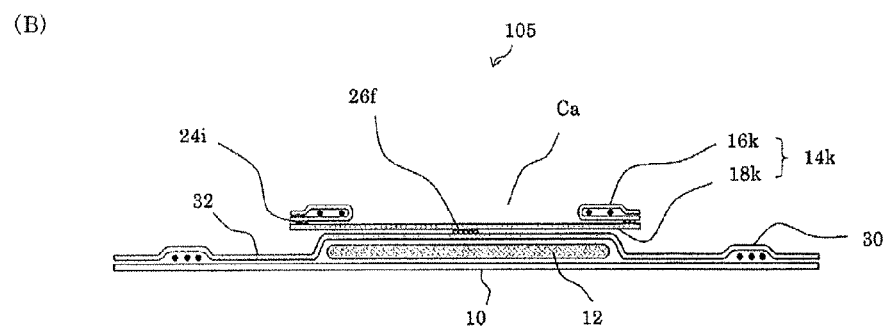

FIG. 19
(A)
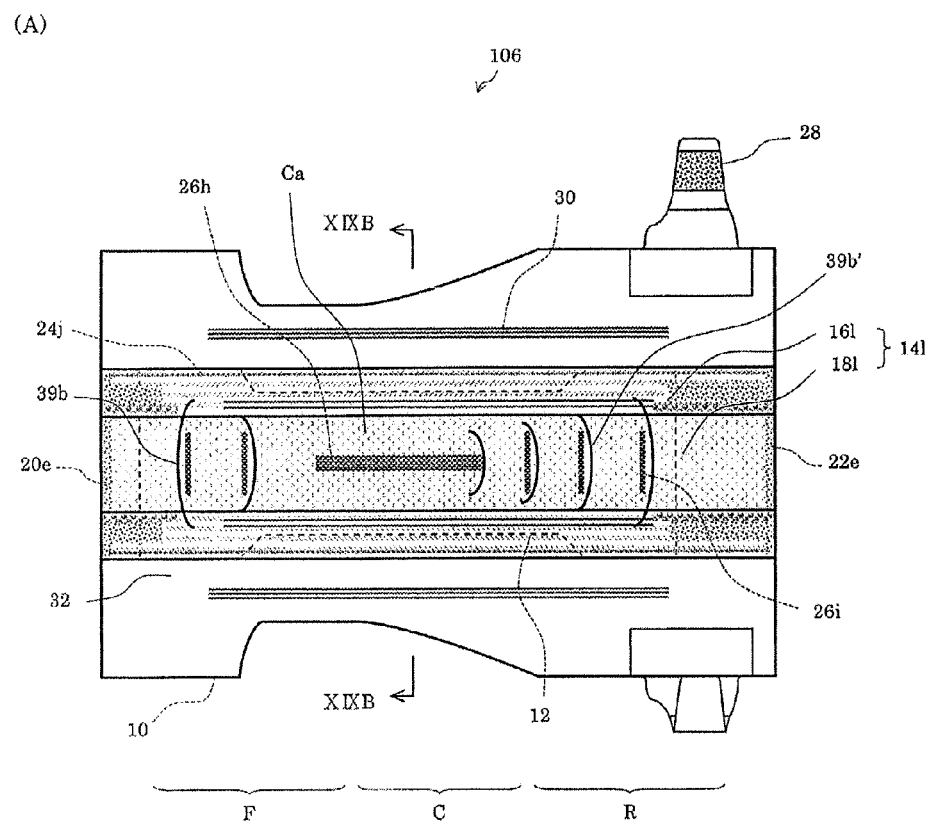
(B)
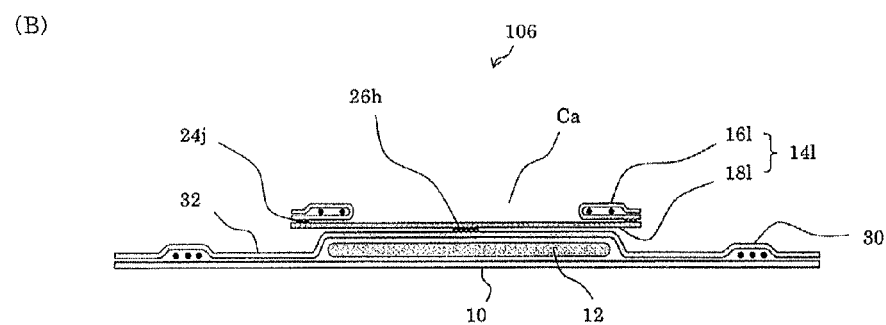

FIG. 20
(A)
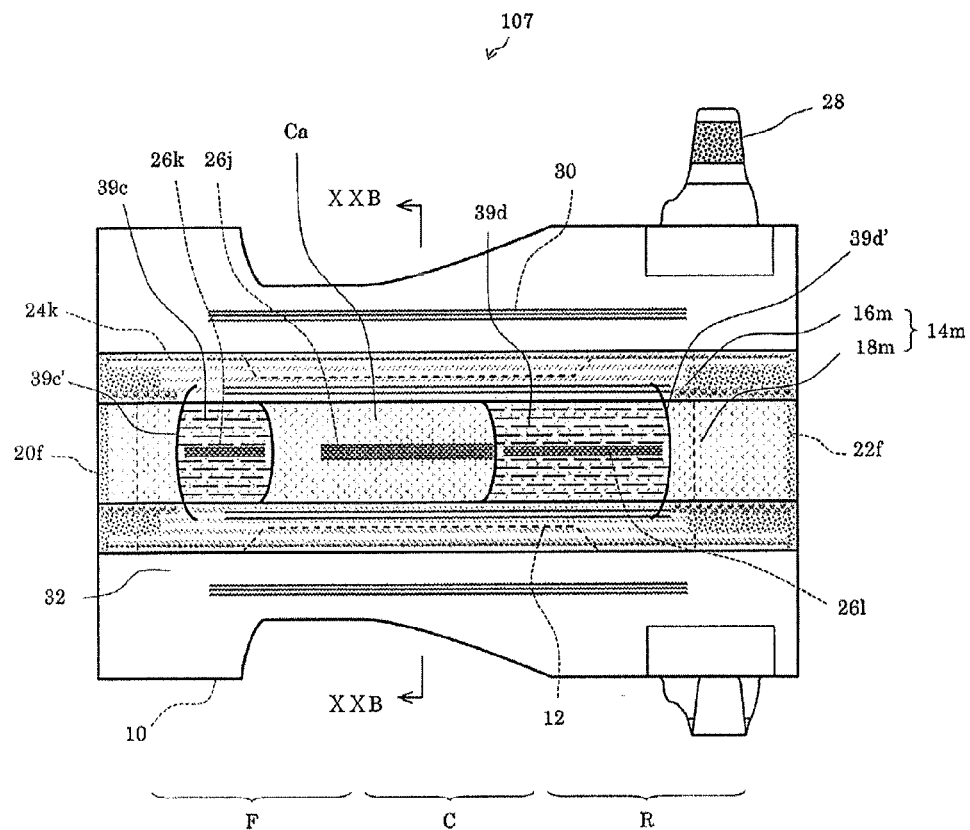
(B)
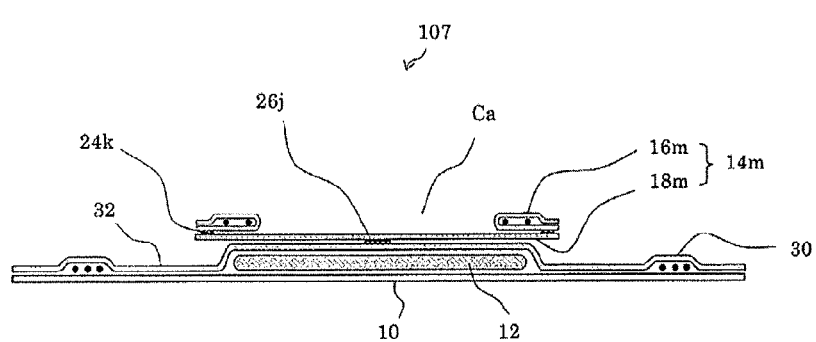

ABSORBENT ARTICLE PROVIDED WITH A BODILY FLUID RECEPTION CANAL

FIELD OF THE INVENTION

The present invention relates to an absorbent article provided with a bodily fluid reception canal.

BACKGROUND ART

Absorbent articles such as paper diapers (disposable diapers) (for infants and adults), sanitary napkins, incontinence articles, training pants or the like are articles that absorb bodily fluids, such as urine excreted from a wearer, by means of an absorber that makes use of a super absorbent polymer (hereinafter referred to as an "SAP"), fluffy pulp or the like.

In conventional absorbent articles, excreted bodily fluid is directly excreted onto the surface of an absorber from the excretory organ and is absorbed into the absorber and fixed thereat through diffusion over the surface of the absorber and transfer from the surface of the absorber to the inside of the absorber. Accordingly, it is necessary to closely attach the absorbent article to the wearer's body so that no gap is formed and to closely attach the surface of the absorber to the wearer's skin, in particular the excretory organ, in order to prevent leakage of bodily fluids from the absorbent article to the exterior.

In order to use such conventional absorbent articles efficiently by fully utilizing the absorption capacity possessed by such absorbent articles, instead of changing the absorbent article each time bodily fluids are excreted, it is necessary to use the absorbent article multiple times, without changing the same even when the bodily fluids are excreted for the first time, so as to continue using the same for the second and/or subsequent excretions of bodily fluids.

However, when the absorbent article is used multiple times, the wearer is inevitably kept in a condition where the skin and the surface of the absorber, which is wet from the bodily fluids, are closely attached over an extended period of time. Such condition where the bodily fluids make contact with the wearer's skin over an extended period of time is not only unpleasant for the wearer but also swells the skin and becomes a cause for bacterial growth that leads to rashes and inflammation.

To remedy the problems associated with the use of such conventional absorbent articles, efforts have been made such as using an air permeable back sheet, improving the surface sheet or the like; however, the actual situation is that, in the end, even when there is still sufficient absorption capacity remaining, the wet condition of the absorber surface is sensed, and the occurrence of skin troubles is avoided by changing to a new absorbent article. For example, with diapers for infants, it is said that an average of only approximately 40% of the absorption capacity is utilized.

SUMMARY OF THE INVENTION

Problems to be Solved by the Invention

In view of the fact that the needs to save resources and conserve energy are demands of the present age, the present inventors contemplated developing an absorbent article which is capable of satisfying both the efficient use of the absorbent article and the prevention of the occurrence of problems due to contact between a bodily fluid and the skin over an extended period of time.

First, in order to clarify the problems, the present inventors conducted specific analysis, by taking a disposable diaper as an example, to see, once again, what the absorbent article is like.

FIG. 28 is a diagram illustrating a life cycle of a disposable diaper.

A life cycle of a disposable diaper contains a string of processes which includes: a wearer wearing an unused disposable diaper; repeating a use cycle consisting of reception of a bodily fluid (urine), distribution of the bodily fluid, and absorption and fixing of the bodily fluid, multiple times (three times in FIG. 28); and removing and disposing the used paper diaper.

The present inventors contemplated this life cycle of the paper diaper and found that the following problems to be solved are present in order to allow for multiple-time repeated use and the provision of both efficiency and comfort.

(A) Problems Regarding Absorption Capacity (a1) Most of the conventional disposable diapers have an absorption capacity which is capable of absorbing, as a theoretical value, an amount of urine that is three times a standard amount of urine; however, since one part of the absorber intensively performs the absorption of urine, the limit for urine leakage is reached faster than the limit based on the theoretical absorption capacity.

(a2) In the conventional disposable diapers, depending on the body position at the time of wearing, a part of the absorber is utilized in a greatly disproportionate manner.

(a3) In the conventional disposable diapers, many troubles occur which are caused, in particular, by the shape of the crotch part and the absorption capacity. A deduction was made that such troubles are caused by the fact that the crotch part: is a part that comes close to the genitalia; is a part with the narrowest width; and is a part required to be constantly flexible in order to closely attach the crotch part to the wearer's body.

(B) Problems that Occur Due to a Wearer's Skin being Exposed to a Moist Condition Over an Extended Period of Time (b1) Measures are needed which can avoid not only the occurrence of rashes but also the conditions in which rashes are likely to occur.

(b2) Means are needed such that even when the absorber absorbs urine to the limit of the absorption capacity and thus, the degree of moisture of the absorber surface is high, the skin is still not wet. More specifically, measures are needed which can prevent the occurrence of the amount of liquid returning to the surface of a level which is not addressable by the conventional dry top sheet.

(b3) Measures are needed, in cases where the absorber surface becomes moist, to avoid the occurrence of friction with respect to the wearer's skin.

Accordingly, it is an object of the present invention to provide an absorbent article which is capable of solving the above-described problems regarding absorption capacity and the above-described problems that occur due to a wearer's skin being exposed to a moist condition over an extended period of time.

Means for Solving the Problems

After finding the problems above and as a result of diligently conducting research, the present inventors have found that: by obtaining a configuration in which the bodily fluid is not directly transferred to the absorber (in particular, the crotch part) and in which the transferred and distribution of the bodily fluid to the front and to the rear can be made regardless of the body position, the entire absorber can be used as evenly as possible such that the absorption capacity can be sufficiently fulfilled (resolution of (a1) above); the influence of disproportionate bodily fluid due to the body position at the time of wearing can be reduced (resolution of (a2) above); and by efficiently using the vicinities of the front end part and the rear end part of the absorber, the bodily fluid does not easily flow into the crotch part (resolution of (a3) above). The present inventors have also found that: by achieving such configuration through the provision of a structure that is capable of receiving the total amount of the excreted bodily fluid and temporarily storing it therein between the surface of the absorber and the wearer's skin, the surface of the absorber and the wearer's skin can constantly be kept in a non-contact state and thus, rashes and the conditions in which rashes are likely to occur can be avoided (achievement of (b1) above); skin-wetting is avoided even when the absorber absorbed urine to the limit of the absorption capacity (achievement of (b2) above); and the generation of friction force between the absorber surface and the wearer's skin is avoided (achievement of (b3) above), and then completed the present invention.

Namely, the present invention provides the following (1) to (19):

(1) An absorbent article including:

an absorbent article body that has a leak preventer in sheet form and an absorber capable of absorbing a bodily fluid, at least one layer thereof being arranged above the leak preventer; and a connection structure that is arranged from a front end part to a rear end part of the absorbent article body in the length direction via a front body, a crotch part and a rear body, the connection structure coupling to the absorbent article body at the front end part and the rear end part, wherein the connection structure has a pair of right and left belt-like supporters and a connection sheet, right and left edge parts thereof respectively coupling to the pair of right and left belt-like supporters, the connection sheet is configured to hang down, on the underside of the belt-like supporters, toward the absorber in the front body, the crotch part and the rear body, so as to form a bodily fluid reception canal with the vicinities of the right and left edge parts of the connection sheet serving as side surfaces and the vicinity of a center part of the connection sheet in the lateral direction serving as a bottom surface, and the bodily fluid reception canal enables the bodily fluid excreted from a wearer to be received and transferred to the absorber.

(2) The absorbent article according to (1), wherein a part of an under surface of the connection sheet configuring the bottom surface of the bodily fluid reception canal and a surface of the absorber are coupled together.

(3) The absorbent article according to (2), wherein a part of the connection sheet configuring the bottom surface has a part that is not coupled to the surface of the absorber in the crotch part.

(4) The absorbent article according to (2) or (3), wherein a part of the connection sheet configuring the bottom surface has a part that is not coupled to the surface of the absorber over the entire width of the bottom surface in the lateral direction, at least at one location in the front-rear direction.

(5) The absorbent article according to any of (1) to (4), wherein the bodily fluid reception canal has an opening at an upper part thereof.

(6) The absorbent article according to any of (1) to (5), wherein the belt-like supporters have stretchability in at least part thereof.

(7) The absorbent article according to any of (1) to (6), wherein the connection sheet that configures the bodily fluid reception canal is provided with a notch that forms an exit for transferring the bodily fluid excreted from the wearer to the absorber.

(8) The absorbent article according to any of (1) to (7), wherein the connection sheet that configures the bodily fluid reception canal is provided with an opening that forms an exit for transferring the bodily fluid excreted from the wearer to the absorber.

(9) The absorbent article according to any of (1) to (8), wherein the connection sheet that configures the bodily fluid reception canal is provided with a slit that forms an exit for transferring the bodily fluid excreted from the wearer to the absorber.

(10) The absorbent article according to any of (1) to (9), wherein part or the entirety of the connection sheet is configured by a hydrophobic non-woven fabric.

(11) The absorbent article according to any of (1) to (9), wherein part or the entirety of the connection sheet is configured by a hydrophilic non-woven fabric.

(12) The absorbent article according to any of (1) to (9), wherein part or the entirety of the connection sheet is configured by a non-woven fabric having both a hydrophobic part and a hydrophilic part.

(13) The absorbent article according to any of (1) to (9), wherein the connection sheet is configured by a liquid-permeable apertured film.

(14) The absorbent article according to any of (1) to (13), wherein the connection structure is coupled to the absorbent article body, at a front end thereof and parts of right and left edges thereof that continue from the front end, such that a front part pocket is formed by the connection structure and the absorbent article body.

(15) The absorbent article according to any of (1) to (14), wherein the connection structure is coupled to the absorbent article body, at a rear end thereof and parts of right and left edges thereof that continue from the rear end, such that a rear part pocket is formed by the connection structure and the absorbent article body.

(16) The absorbent article according to any of (1) to (15), wherein a degree of hanging (h/w) of the bodily fluid reception canal decreases from the crotch part to the rear body, the degree of hanging being a ratio of a distance (h) between a plane connecting upper surfaces of the band-like supporters and a bottom surface of the connection sheet with respect to an inner interval (w) between the pair of right and left belt-like supporters.

(17) The absorbent article according to any of (1) to (16), wherein a degree of hanging (h/w) of the bodily fluid reception canal decreases from the crotch part to the front body, the degree of hanging being a ratio of a distance (h) between a plane connecting upper surfaces of the band-like supporters and a bottom surface of the connection sheet with respect to an inner interval (w) between the pair of right and left belt-like supporters.

(18) The absorbent article according to any of (1) to (17), wherein inner leg gathers are further provided on exterior sides of the bodily fluid reception canal in the lateral direction.

(19) The absorbent article according to any of (1) to (18), wherein outer leg gathers are further provided on right and left edge parts of the absorbent article body.

Effect of the Invention

An absorbent article according to the present invention is capable of sufficiently fulfilling absorption capacity of an absorber, and a wearer's skin will not be exposed to a moist condition over an extended period of time and thus, problems such as the occurrence of rashes or the like are suppressed.

BRIEF DESCRIPTIONS OF THE DRAWINGS

FIG. 1 contains schematic diagrams illustrating an example of an absorbent article according to the present invention.

FIG. 2 contains schematic diagrams illustrating a connection structure used in an absorbent article.

FIG. 3 contains schematic lateral end views illustrating various examples of connection structures.

FIG. 4 contains schematic diagrams illustrating various states of formation of a bodily fluid reception canal.

FIG. 5 contains schematic diagrams illustrating various states of formation of a bodily fluid reception canal.

FIG. 6 contains schematic diagrams illustrating various states of formation and arrangements of a bodily fluid reception canal.

FIG. 7 contains schematic plan views illustrating examples of a connection sheet provided with various notches.

FIG. 8 contains schematic plan views illustrating examples of a connection sheet provided with various openings.

FIG. 9 contains schematic plan views illustrating examples of a connection sheet provided with various slits.

FIG. 10 contains schematic plan views illustrating examples of a connection sheet provided with various exits.

FIG. 11 is a schematic diagram illustrating an example of a state of arrangement of belt-like supporters in an absorbent article.

FIG. 12 contains schematic lateral end views illustrating examples of various belt-like supporters.

FIG. 13 contains schematic diagrams illustrating an embodiment of an absorbent article according to the present invention.

FIG. 14 contains schematic diagrams illustrating a connection structure.

FIG. 15 contains schematic diagrams illustrating another embodiment of an absorbent article according to the present invention.

FIG. 16 contains schematic diagrams illustrating a further embodiment of an absorbent article according to the present invention.

FIG. 17 contains schematic diagrams illustrating an example of a conventional absorbent article.

FIG. 18 contains schematic diagrams illustrating a further embodiment of an absorbent article according to the present invention.

FIG. 19 contains schematic diagrams illustrating a further embodiment of an absorbent article according to the present invention.

FIG. 20 contains schematic diagrams illustrating a further embodiment of an absorbent article according to the present invention.

EMBODIMENTS OF THE INVENTION

Hereinafter, the absorbent article according to the present invention will be described in detail, based on the preferred embodiments illustrated in the attached drawings. It should be noted that, in the present specification, when the absorbent article according to the present invention is actually worn, a side close to the skin of the wearer will be referred to as the "top" and a side far therefrom will be referred to as the "bottom/under." In addition, when the absorbent article according to the present invention is actually worn, a side corresponding to the front side of the wearer's body will be referred to as the "front" and a side corresponding to the back side thereof will be referred to as the "rear." Moreover, in order to facilitate understanding, in the respective drawings, members that are actually in contact with each other may be illustrated such that they are spaced apart. In the respective plan views among the attached drawings, the front side of the absorbent article or the like is shown to be positioned at the left side of the corresponding drawing.

In addition, in the present specification, an "absorbent article body" collectively refers to a leak preventer, a top sheet that can be provided above the leak preventer and various other members that can be provided to the absorbent article, all of which are constituent members of the absorbent article. In accordance with this, when the absorbent article is a diaper, the absorbent article body will be referred to as a diaper body.

Moreover, in the present specification, an "absorber surface" refers to a surface of an absorber when it is exposed, and to a surface of a diffusion sheet, acquisition sheet, top sheet (surface sheet) or the like when the absorber is covered with such diffusion sheet, acquisition sheet, top sheet (surface sheet) or the like.

Figure 1:
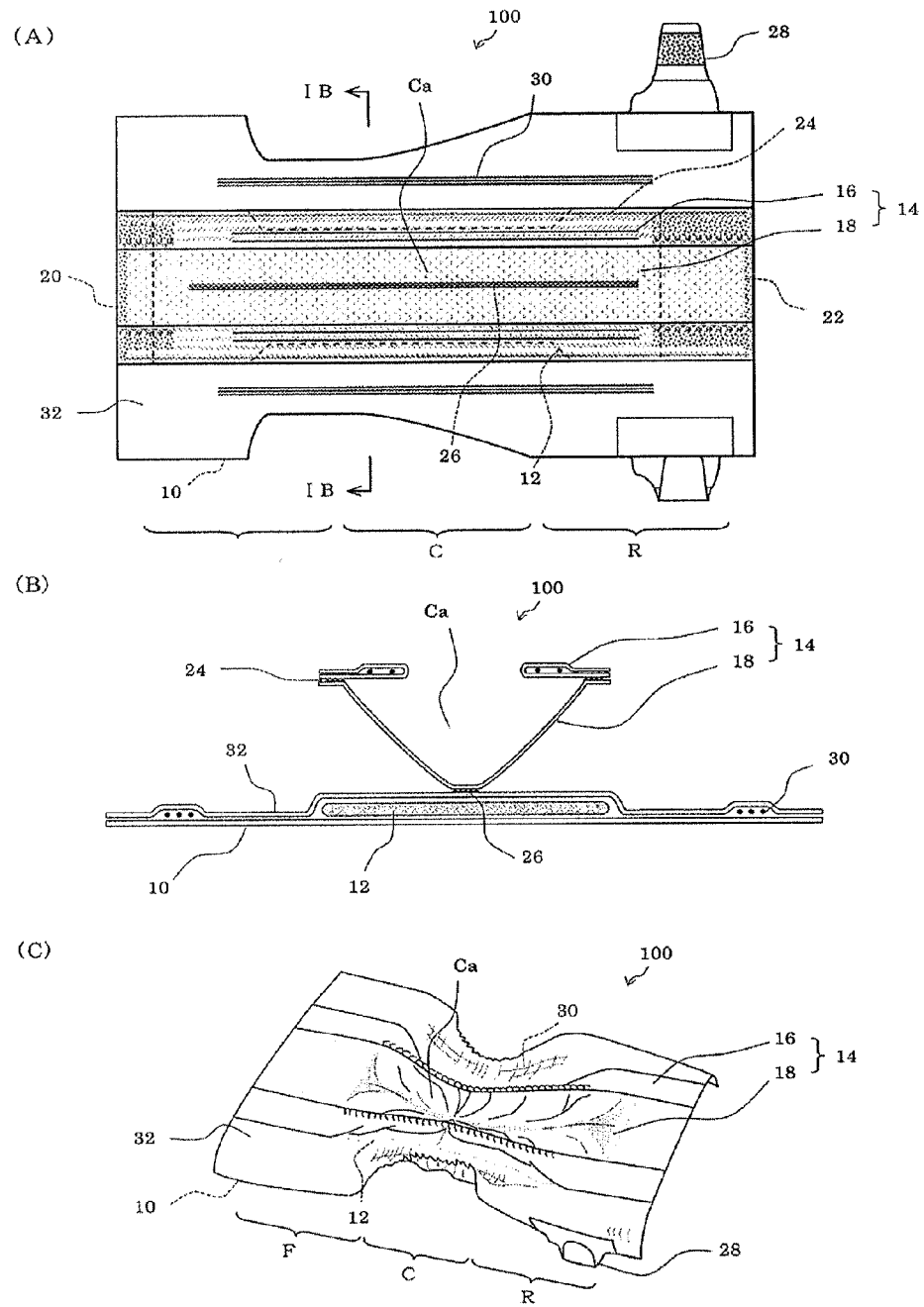

FIG. 1 contains schematic diagrams illustrating an example of an absorbent article according to the present invention. FIG. 1(A) is a developed plan view which schematically shows the state in which stress is applied to an absorbent article, in the form of a tape-type diaper, such that it is pulled in the front-rear direction and the lateral direction so as to be developed into a substantially planar form. FIG. 1(B) is a lateral end view along line IB-IB in FIG. 1(A) of the case where stress is not applied to the absorbent article (i.e. in a relaxed state). FIG. 1(C) is a perspective view of the case where stress is not applied to the absorbent article (i.e. in a relaxed state).

Absorbent article 100 according to the present invention shown in FIG. 1 is configured as a tape-type diaper, and is basically provided with: an absorbent article body including leak preventer 10 in sheet form and absorber 12 capable of absorbing a bodily fluid, wherein at least one layer thereof is arranged above leak preventer 10; and connection structure 14 that is arranged from a front end part to a rear end part of the absorbent article body in the length direction, via front body F, crotch part C and rear body R, the connection structure coupling to the absorbent article body at the front end part and the rear end part thereof.

Materials that are generally used as a back sheet can be used for the materials of leak preventer 10. In particular, a resin film made of, for example, PE, PP, PET, EVA or the like and a bodily fluid impermeable sheet such as a foam sheet made of the resin described above can be used. For the bodily fluid impermeable sheet, a sheet having air permeability, such as an air permeable sheet or the like may also be preferably used.

In addition, when the above-described resin film is used, a multilayered sheet of such film and a non-woven fabric may be used in order to improve the texture and appearance. In this case, a spunbond (SB) or thermalbond non-woven fabric (for example, an air-through type) having a relatively low basis weight or the like may preferably be used as the non-woven fabric.

Moreover, a multilayered sheet of such resin film and an absorber in sheet form, which is described below, may also be used.

Further, a high water-resistant non-woven fabric may also be used. Examples of such high water-resistant non-woven fabric include an SMS non-woven fabric having a degree of water resistance of 100 mm $H_2O$ or more and an SMS non-woven fabric in which pores in a non-woven web are filled with microfibrillated cellulose (MFC) or wax so as to provide such fabric with water resistance. In this case, a high water-resistant non-woven fabric may be used alone or may also be used as a multilayered sheet of the film and such high water-resistant non-woven fabric.

Leak preventer 10 may be configured from a plurality of members.

Leak preventer 10 is in sheet form; however, it is not particularly limited in terms of shape as long as it accommodates absorber 12, or the like, above itself and is capable of being arranged with connection structure 14 thereon.

Absorber 12 used in the present invention is not particularly limited, as long as it is capable of absorbing bodily fluid, and any absorber used in publicly known conventional absorbent articles may be used. Examples such as: pulverized wood pulp; an absorber in which pulverized wood pulp and flake-shape or powdery SAP are mixed and shaped into a mat; a sheet-like absorber formed into a thin sheet and having SAP as a primary component, or the like, may be used. These absorbers keep the shape thereof and at the same time prevent the generation and droppage of fine powder generating from pulp and SAP. Thus, in general, the absorbers are covered with a core wrapping material made of tissue paper, a non-woven fabric, a perforated film, or the like. In the present specification, when a core wrapping material is used, such core wrapping material is also inclusively referred to as an "absorber."

An absorber in sheet form excels in morphological stability and capability of SAP fall prevention, etc.

Among various types of absorber in sheet form, a super absorbent sheet containing 50 weight % or more, preferably 60 weight % or more, or more preferably 70 weight % or more of SAP is preferred. In addition, from the perspective of stability, etc. of the super absorbent sheet, the content of SAP therein is preferably 95 weight % or less.

The super absorbent sheet is an extremely-thin absorber in sheet form having SAP as a primary component. Since the content of SAP is extremely high, the thickness of the super absorbent sheet is extremely low. The thickness of the super absorbent sheet is preferably 1.5 mm or less and more preferably 1 mm or less.

The super absorbent sheet is not particularly limited in terms of its configuration and production method, as long as it is an extremely-thin absorber in sheet form having SAP as a primary component.

For example, there is a super absorbent sheet obtained by an Air-Laid process. In the Air-Laid process, pulverized wooden pulp and SAP are mixed and a binder is added to shape the mixture into a sheet form and then a super absorbent sheet is obtained. As examples of a super absorbent sheet obtained through this process, NOVATHIN (US trademark) manufactured by Rayonier Inc. in the US and B-SAP manufactured by Oji Kinocloth Co., Ltd. are known.

Another example of the super absorbent sheet includes a super absorbent sheet obtained through a process involving coating a bodily fluid permeable sheet such as a non-woven fabric with SAP-dispersed slurry. Here, the SAP-dispersed slurry is preferably prepared by dispersing SAP and microfibrillated cellulose (MFC) in a mixed solvent of water and ethanol. As an example of the super absorbent sheet obtained through this process, MegaThin (trademark) manufactured by Japan Absorber Technology Institute is known.

Other examples of the super absorbent sheet include: a super absorbent sheet obtained through a process involving having a raised non-woven fabric carry a large amount of SAP and fixing the SAP with a hot melt binder, an emulsion binder, an aqueous fiber, or the like; a super absorbent sheet obtained through a process involving mixing fibrous SAP with a PET (polyethylene terephthalate) fiber and forming the mixture into a web; and an SAP sheet obtained by sandwiching an SAP layer with tissues from above and below.

At least one layer of absorber 12 is arranged above leak preventer 10. Namely, absorber 12 may be comprised of one layer or two or more layers (multilayer).

In addition, absorber 12 may be arranged in a folded condition.

The absorbent article body includes above-described leak preventer 10 and absorber 12 and may also include other constituent members.

Connection structure 14 is arranged from the front end part to the rear end part of the absorbent article body in the length direction via front body F, crotch part C and rear body R. A front end part and a rear end part of connection structure 14 are respectively coupled to the front end part and the rear end part of the absorbent article body at front end coupling part 20 and rear end coupling part 22. The method of coupling is not particularly limited, and they may be coupled using, for example, a hot melt adhesive, a heat sealed bond or the like.

Connection structure 14 includes a pair of right and left belt-like supporters 16 and connection sheet 18, the right and left edge parts thereof respectively coupling to the pair of right and left belt-like supporters 16. The upper surfaces of the right and left edge parts of connection sheet 18 are coupled to the underside of the pair of right and left belt-like supporters 16 at coupling parts 24.

Belt-like supporter 16 is configured by covering the top and the bottom of two parallel polyurethane filaments with non-woven fabrics. Accordingly, belt-like supporter 16 has stretchability and cushioning properties.

As shown in FIG. 1(B), connection sheet 18 is configured to hang down toward absorber 12 on the underside of belt-like supporters 16 in front body F, crotch part C and rear body R.

As shown in FIG. 1(B), connection sheet 18 forms bodily fluid reception canal Ca, with the vicinities of the right and left edge parts of the connection sheet serving as side surfaces and the vicinity of the center part in the lateral direction thereof serving as a bottom surface.

As shown in FIG. 1(B), in absorbent article 100, a part of the under surface of connection sheet 18, which configures the bottom surface of bodily fluid reception canal Ca, and a surface of absorber 12 are coupled together at coupling part 26.

In addition, as shown in FIG. 1(B), in absorbent article 100, the part of connection sheet 18, which configures the bottom surface of bodily fluid reception canal Ca, has a part which is not coupled to the surface of absorber 12 in crotch part C. In this way, the shape of bodily fluid reception canal Ca is less likely to be affected by way of the movement or deformation of absorber 12 due to the movement, etc. of the wearer. Accordingly, in one of the preferred embodiments of the invention, the part of the connection sheet which configures the bottom surface has a part which is not coupled to the absorber surface in the crotch part.

In addition, as shown in FIG. 1(A), in absorbent article 100, the part of connection sheet 18 which configures the bottom surface has a part which is not coupled to the surface of absorber 12 over the entire width of the bottom surface in the lateral direction, at least one location in the front-rear direction. More specifically, in front of and behind coupling part 26, the part of connection sheet 18 which configures the bottom surface is not coupled to the surface of absorber 12 over the entire width of the bottom surface in the lateral direction. In this way, by connection sheet 18 having parts that keep a spaced-apart condition at positions in front of and behind coupling part 26, the bottom surface of connection sheet 18 that connects to the front end part and the rear end part floats and thus, the slope angle of the bottom surface toward crotch part C can be increased. As a result, leakage from the front end and the rear end of the absorbent article body can be suppressed by reducing the amount of bodily fluids reaching to the front end and the rear end thereof. Accordingly, in one of the preferred embodiments of the present invention, the part of the connection sheet which configures the bottom surface has a part which is not coupled to the absorber surface over the entire width of the bottom surface in the lateral direction, at least one location in the front-rear direction.

Coupling part 26 is linearly provided, at the center position of connection sheet 18 in the lateral direction, from a part of front body F to a part of rear body R via crotch part C (see FIG. 1(A)). The method of coupling a part of the under surface of connection sheet 18 and the surface of absorber 12 is not particularly limited, and they may be coupled using, for example, a hot melt adhesive, a heat sealed bond or the like.

In absorbent article 100, bodily fluid reception canal Ca assumes a symmetrical V-shape and has a configuration with an opening since the space between the pair of right and left belt-like supporters 16 is open.

At the time of wearing, the only region of absorbent article 100 that makes direct contact with the wearer's skin is the upper surfaces of belt-like supporters 16, which are present in a floating condition at both edges of bodily fluid reception canal Ca, and the urine excretory organ and the anus are both accommodated in the opening between the pair of right and left belt-like supporters 16.

Accordingly, when the wearer excretes urine, the total amount of the excreted urine is first accommodated in bodily fluid reception canal Ca and thus, urine is not directly excreted onto the surface of absorber 12.

Subsequently, the urine stored in bodily fluid reception canal Ca is distributed and supplied onto the surface of absorber 12 from an exit for bodily fluids.

In absorbent article 100, the exit is not explicit in bodily fluid reception canal Ca; however, connection sheet 18 is configured by a hydrophilic non-woven fabric and is liquid permeable, and multiple fine pores in this non-woven fabric serve as the exit for bodily fluids. Accordingly, the urine stored in bodily fluid reception canal Ca is then distributed and supplied onto the surface of absorber 12 through such multiple fine pores.

An example of such hydrophilic non-woven fabric includes a PE/PP-based spunbond non-woven fabric (manufactured by, for example, Chisso Corporation and having a basis weight of 15 $g/m^2$), which is provided with liquid permeability by treatment using a hydrophilization treatment agent, may be used.

Accordingly, in one of the preferred embodiments of the present invention, part or the entirety of the connection sheet is configured by a hydrophilic non-woven fabric.

As described above, bodily fluid reception canal Ca allows the reception of the bodily fluids excreted from the wearer and the transfer thereof to absorber 12. In addition, the bodily fluids transfer within bodily fluid reception canal Ca and are distributed to absorber 12 through the exits of bodily fluid reception canal Ca.

At the time of wearing absorbent article 100, not only for the first excretion of urine but also for the second and later excretions, the total amount of the excreted urine is first accommodated in bodily fluid reception canal Ca and is not directly excreted onto the surface of absorber 12.

Accordingly, from the start to the end of wearing, bodily fluid reception canal Ca serves as a barrier and thus, the wearer's skin does not become wet through contact between the wearer's skin and the surface of absorber 12.

In absorbent article 100, the total amount of the excreted bodily fluids is accommodated by bodily fluid reception canal Ca and is temporarily stored therein. Thereafter, the bodily fluids leach out from a relatively broad area of connection sheet 18, since connection sheet 18 has liquid permeability over its entirety, and are then supplied onto the surface of absorber 12. At this time, the body position at the time of wearing, the excretion speed, the excretion amount or the like may have an influence; however, a relatively broad part of absorber 12 can be utilized and thus, the load on the part of crotch part C is significantly suppressed.

It should be noted that when the wearer excretes feces, liquid components in the feces transfer from the fine pores in connection sheet 18 onto the surface of absorber 12; however, the total amount of solid components stay within bodily fluid reception canal Ca.

As shown in FIG. 1(C), bodily fluid reception canal Ca in absorbent article 100 is formed such that the width in the lateral direction is small and the depth in the vertical direction is deep in crotch part C, and such that the width in the lateral direction gradually increases and the depth in the vertical direction gradually becomes shallow from crotch part C to each of front body F and rear body R.

The present invention is not limited to the above-described configuration and, for example, various publicly-known conventional members may be provided.

In addition to the members described above, absorbent article 100 is provided with various other members described below.

Detachable members 28 are provided on both the right and left sides of leak preventer 10 in the vicinity of the rear end thereof. On the under surface of leak preventer 10 in the vicinity of the front end thereof, detachable members (not shown) are provided such that they can be detached from detachable members 28. These detachable members may be configured by, for example, various hook-and-loop fasteners. In particular, as for detachable members 28 provided on both the right and left sides of leak preventer 10 in the vicinity of the rear end thereof, Velcro tapes (male) may be used. As for the detachable members provided on the under surface of leak preventer 10 in the vicinity of the front end, TLZs (female) may be used.

In addition, absorbent article 100 is provided with outer leg gathers (OLGs) 30 on the right and left edge parts of the absorbent article body. OLG 30 is formed by three parallel polyurethane filaments (stretchable members) arranged between leak preventer 10 and top sheet 32. Top sheet 32 is not particularly limited, and any publicly-known conventional top sheet may be used.

The absorbent article according to the present invention may be provided with inner leg gathers (ILGs) outward in the lateral direction of bodily fluid reception canal Ca. The absorbent article according to the present invention may be provided with both OLGs and ILGs. The ILGs are gathers having a pair of right and left head parts and leg parts. Since the leg parts are present by being coupled to the right and left edges of the absorber surface or the right and left edges of the absorbent article body, they may also be referred to as standing leg gathers (SLGs).

The connection structure used in the absorbent article according to the present invention will be described in detail below.

FIG. 2 contains schematic diagrams illustrating connection structure 14 used in absorbent article 100. FIG. 2(A) is a plan view and FIG. 2(B) is a lateral end view.

Connection structure 14 includes belt-like supporters 16 and connection sheet 18. Connection structure 14 can be obtained, for example, by coupling the right and left edges of connection sheet 18 to belt-like supporters 16. The method of coupling is not particularly limited, and they may be coupled using, for example, a hot melt adhesive, a heat sealed bond or the like.

In absorbent article 100, connection structure 14 shown in FIG. 2 is provided such that bodily fluid reception canal Ca is formed (see FIG. 1).

Hereinafter, first, the connection sheet will be described.

The material of the connection sheet is not particularly limited; however, preferable examples include: a synthetic resin film, a perforated sheet and a net-like sheet made of PE, PP, PET, polyurethane, SBR-based rubber, PVA, EVA or the like; a dry non-woven fabric, a wet non-woven fabric, a spunbond non-woven fabric and a spunmelt non-woven fabric (represented by a spunbond/melt-blown/spunbond laminated body) containing, as constituent components, synthetic fiber such as PE fiber, PP fiber, PET fiber, PE/PP composite fiber, PE/PET composite fiber or the like; and a dry non-woven fabric, a wet non-woven fabric and a spunbond non-woven fabric containing, as constituent components, hydrophilic fiber having cellulose such as wood pulp, cotton, rayon, lyocell or acetate as a primary component.

The basis weight of the connection sheet is preferably approximately 5 to 50 g/m² and the connection sheet is preferably a flexible and relatively thin sheet.

Figure 3:
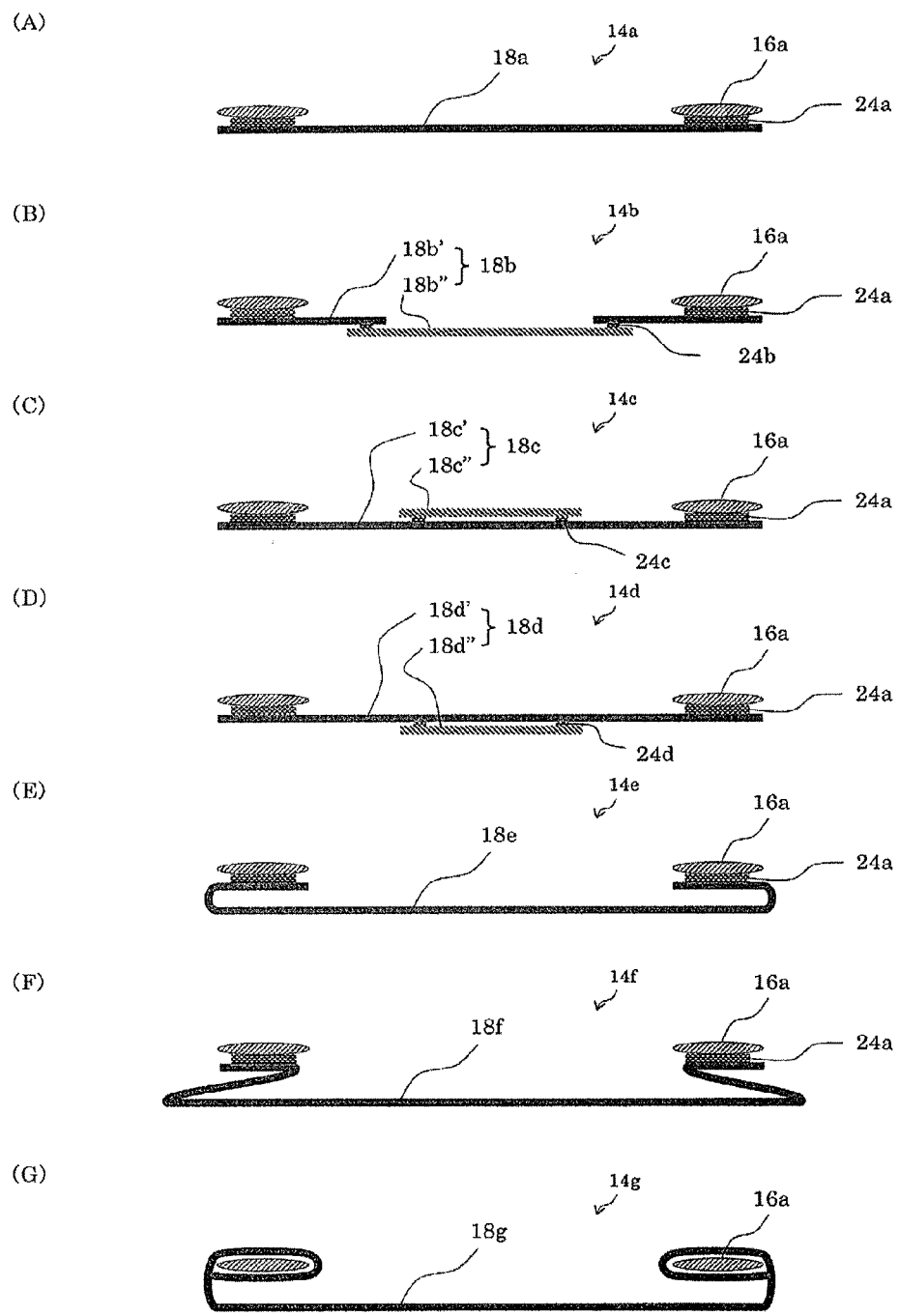

FIG. 3 contains schematic lateral end views illustrating various examples of connection structures.

Connection structure 14a shown in FIG. 3(A) is configured by belt-like supporters 16a and connection sheet 18a being coupled together at coupling parts 24a.

As for belt-like supporters 16a, belt-like supporters similar to belt-like supporters 16 in connection structure 14 shown in FIG. 2 may be used. The same applies to the respective belt-like supporters 16a in FIGS. 3(B) to 3(G).

Connection sheet 18a is a single layer and the material thereof is not particularly limited, and it can be configured by the above-described materials. The connection sheet in this form has advantages to the effect that the configuration is simple and that the production process can be simplified. It should be noted that a hydrophobic non-woven fabric (for example, a PE/PP-based spunbond non-woven fabric) having a part thereof (for example, only the center part) applied with hydrophilic treatment (for example, treatment with a surfactant) may be used as the connection sheet.

Connection structure 14b shown in FIG. 3(B) is configured by the pair of right and left belt-like supporters 16a and connection sheet 18b being coupled together at coupling parts 24a. Connection sheet 18b is configured by two right and left hydrophobic sheets 18b' and hydrophilic sheet 18b" in the center in the lateral direction being coupled together at coupling parts 24b. The production process of the connection sheet in this form is slightly complex as compared to that of connection sheet 18a shown FIG. 3(A); however, this connection sheet has the advantage of manifesting various capabilities by the combination of various hydrophobic sheets and various hydrophilic sheets.

Connection structure 14c shown in FIG. 3(C) is configured by the pair of right and left belt-like supporters 16a and connection sheet 18c being coupled together at coupling parts 24a. Connection sheet 18c is configured by hydrophilic sheet 18c" being arranged in the center in the lateral direction on the upper surface of hydrophobic sheet 18c' and by being coupled together at coupling parts 24c. Connection sheet 18c has a double structure in the center part. The material cost of the connection sheet in this form is higher as compared to that of connection sheet 18b shown in FIG. 3(B); however, this connection sheet has the advantage of the production process being simple.

Connection structure 14d shown in FIG. 3(D) is configured by the pair of right and left belt-like supporters 16a and connection sheet 18d being coupled together at coupling parts 24a. Connection sheet 18d is configured by hydrophobic sheet 18d" being arranged in the center in the lateral direction on the under surface of hydrophilic sheet 18d' and by being coupled together at coupling parts 24d. Connection sheet 18d has a double structure in the center part. The material cost of the connection sheet in this form is higher as compared to that of connection sheet 18b shown in FIG. 3(B); however, this connection sheet has the advantage of the production process being simple.

Connection structure 14e shown in FIG. 3(E) is configured by the pair of right and left belt-like supporters 16a and connection sheet 18e being coupled together at coupling parts 24a with the right and left edges of connection sheet 18e being folded inward on the upper side. The connection sheet in this form (i.e. the folded-back connection sheet) has the advantage of the bodily fluid storage capacity being able to be increased since the width in the lateral direction can be increased and thus, the volume of bodily fluid reception canal Ca can also be increased.

Connection structure 14*f* shown in FIG. 3(F) is configured by the pair of right and left belt-like supporters 16*a* and connection sheet 18*f* being coupled together at coupling parts 24*a* with the right and left edges of connection sheet 18*f* being folded inward and then further being folded outward on the upper side. The connection sheet in this form (i.e. the collapsible connection sheet) has the advantage of the bodily fluid storage capacity being able to be further increased since the width in the lateral direction can be further increased and thus, the volume of bodily fluid reception canal Ca can also be further increased.

Connection structure 14*g* shown in FIG. 3(G) is configured by the pair of right and left belt-like supporters 16*a* and connection sheet 18*g* being integrated together with the right and left edges of connection sheet 18*g* respectively wrapping the pair of right and left belt-like supporters 16*a* on the upper side. In the connection sheet in this form, even when the surfaces of the belt-like supporters are uneven or hard, since such belt-like supporters are covered by the connection sheet, the touch felt by the wearer can be improved by the softness and smoothness of the connection sheet. In addition, the amount of adhesives used for coupling can be reduced.

A form in which part or the entirety of the connection sheet is configured by a hydrophobic non-woven fabric, a form in which part or the entirety of the connection sheet is configured by a hydrophilic non-woven fabric and a form in which part or the entirety of the connection sheet is configured by a non-woven fabric having both a hydrophobic part and a hydrophilic part, are all preferred embodiments of the present invention.

Next, states of formation of bodily fluid reception canal Ca will be described.

As described above, the width in the lateral direction and the depth in the vertical direction of bodily fluid reception canal Ca in absorbent article 100 vary depending on the position in the front-rear direction.

Connection sheet 18 hangs down by its own weight from belt-like supporters 16. The degree of hanging increases as the width in the lateral direction decreases. In the lateral direction, the degree of hanging is large at the center position which is farthest from belt-like supporters 16. When the width of belt-like supporter 16 in the lateral direction is forcibly decreased or stress is applied to connection sheet 18, the degree of hanging can be further increased.

FIG. 4 contains schematic diagrams illustrating various states of formation of the bodily fluid reception canal. FIG. 4 only shows the connection structure and the absorber in lateral end views, and other members are omitted.

The respective connection structures 14*a* shown in FIGS. 4(A) to 4(C) correspond to the connection structure shown in FIG. 3(A).

Connection sheet 18*a* is configured to hang down toward absorber 12*a* on the underside of belt-like supporters 16*a*, and bodily fluid reception canal Ca is formed with the vicinities of the right and left edge parts of connection sheet 18*a* serving as the side surfaces and the vicinity of the center part of connection sheet 18*a* in the lateral direction serving as the bottom surface.

In the present invention, the degree of hanging of the connection sheet is expressed by the ratio of a distance h between the plane connecting the upper surfaces of the band-like supporters and the bottom surface of the connection sheet with respect to an inner interval w between the pair of right and left belt-like supporters: degree of hanging=h/w.

In FIG. 4(A), the under surface of connection sheet 18*a* which configures the bottom surface of bodily fluid reception canal Ca is not coupled to absorber 12*a* and is spaced apart therefrom.

Bodily fluid reception canal Ca shown in FIG. 4(A) is in a relaxed state, in which stress is not applied, and thus, the depth is shallow and the degree of hanging ($h_0/w_0$) of connection sheet 18*a* is approximately between 0.1 and 0.4.

In FIG. 4(B), the under surface of connection sheet 18*a* which configures the bottom surface of bodily fluid reception canal Ca is coupled and fixed to absorber 12*a* at two coupling parts 26*a* on the right and left thereof. In this way, bodily fluid reception canal Ca is formed with a large bottom surface width in the lateral direction. The inner surface of bodily fluid reception canal Ca is U-shaped. The degree of hanging ($h_1/w_1$) of connection sheet 18*a* is approximately between 0.3 and 0.8.

Accordingly, by coupling and fixing the under surface of the connection sheet to the absorber surface as described above, the degree of hanging can be increased as compared to the case in which no coupling is performed.

In FIG. 4(C), the under surface of connection sheet 18*a* which configures the bottom surface of bodily fluid reception canal Ca is coupled and fixed to absorber 12*a* at coupling part 26*b* in the center in the lateral direction. In this way, bodily fluid reception canal Ca is formed with a small width in the lateral direction but a large depth in the vertical direction. The inner surface of bodily fluid reception canal Ca is V-shaped. The degree of hanging ($h_2/w_2$) of connection sheet 18*a* is approximately between 1.5 and 2.0 at a maximum.

As described above, the degree of hanging is an indicator of the depth of bodily fluid reception canal Ca as well as an indicator of the degree of the belt-like supporters present on both edges of the connection structure floating from the absorber surface. Namely, the larger the degree of hanging, the larger the spaced-apart distance between the belt-like supporters and the absorber surface. In association thereto, the spaced-apart distance between the wearer's skin surface and the absorber surface is increased, and thus a barrier effect (an effect of preventing contact between the wearer's skin and the absorber surface) is also enhanced.

According to the present invention, in one of the preferred embodiments, the degree of hanging h/w decreases from crotch part C toward rear body R. In such embodiment, bodily fluid reception canal Ca is narrow and deep in crotch part C but is wide and shallow in rear body R, and thus, the reception of feces into bodily fluid reception canal Ca is performed smoothly.

In addition, according to the present invention, in one of the preferred embodiments, the degree of hanging h/w decreases from crotch part C toward front body F. In such embodiment, bodily fluid reception canal Ca is narrow and deep in crotch part C but is wide and shallow in front body F, and thus, the urine excretory organ can be easily and appropriately positioned in bodily fluid reception canal Ca.

Such state of formation of bodily fluid reception canal Ca may be used alone or a plurality of such states of formation may be used in a single absorbent article.

For example, three types of states of formation may be used. At positions in the vicinity of the front end part of front body F and in the vicinity of the rear end part of rear body R, a floated state as shown in FIG. 4(A) may be used. At positions in front body F and rear body R in the vicinities in front of and behind crotch part C (i.e. in the vicinities of the urine excretory organ and the feces excretory organ (i.e. the anus)), a state as shown in FIG. 4(B) may be used, in which the bottom surface with a wide width is present. At crotch part C, which is a re-narrowed region, a state as shown in FIG. 4(C) may be used, in which the width is small, the inner surface assumes a V-shape with a large depth, and the degree of separation of belt-like supporters 16a from the surface of absorber 12a is large.

In addition, two types of states of formation may also be used. In particular, the state shown in FIG. 4(A) and the state shown in FIG. 4(B) may be combined. The state shown in FIG. 4(A) and the state shown in FIG. 4(C) may be combined. Further, the state shown in FIG. 4(B) and the state shown in FIG. 4(C) may be combined.

FIG. 5 contains schematic diagrams illustrating various states of formation of the bodily fluid reception canal. FIG. 5 only shows the connection sheet in a lateral end view and other members are omitted.

All FIGS. 5(A) to 5(D) show the forms of a basic bodily fluid reception canal.

The connection sheet shown in FIG. 5(A) forms a U-shaped bodily fluid reception canal in a similar manner to that of the connection sheet shown in FIG. 4(B).

The connection sheet shown in FIG. 5(B) forms a V-shaped bodily fluid reception canal in a similar manner to that of the connection sheet shown in FIG. 4(C).

The connection sheet shown in FIG. 5(C) forms a U-shaped bodily fluid reception canal with the width of the bottom surface being large and such width decreasing in an upward direction (i.e. a wide-based U-shaped bodily fluid reception canal).

The connection sheet shown in FIG. 5(D) forms a U-shaped bodily fluid reception canal with the width of the bottom surface being small and such width increasing in an upward direction (i.e. a narrow-based U-shaped bodily fluid reception canal).

All FIGS. 5(E) to 5(J) show combinations of the above-described forms of the basic bodily fluid reception canal.

The connection sheet shown in FIG. 5(E) forms a bodily fluid reception canal that includes both a V-shaped part and a U-shaped part.

The connection sheet shown in FIG. 5(F) forms a bodily fluid reception canal that includes both a V-shaped part and a wide-based U-shaped part.

The connection sheet shown in FIG. 5(G) forms a bodily fluid reception canal that includes both a V-shaped part and a narrow-based U-shaped part.

The connection sheet shown in FIG. 5 (H) forms a bodily fluid reception canal that includes both a U-shaped part and a wide-based U-shaped part.

The connection sheet shown in FIG. 5 (I) forms a bodily fluid reception canal that includes both a U-shaped part and a narrow-based U-shaped part.

The connection sheet shown in FIG. 5(J) forms a bodily fluid reception canal that includes both a wide-based U-shaped part and a narrow-based U-shaped part.

These are preferred examples of the forms of the bodily fluid reception canal and they can be appropriately selected depending on the diaper size, or whether or not the diaper is an underpants-type or a tape-type.

In addition, in the present invention, forms and/or combinations other than the above may also be used.

Figure 6:
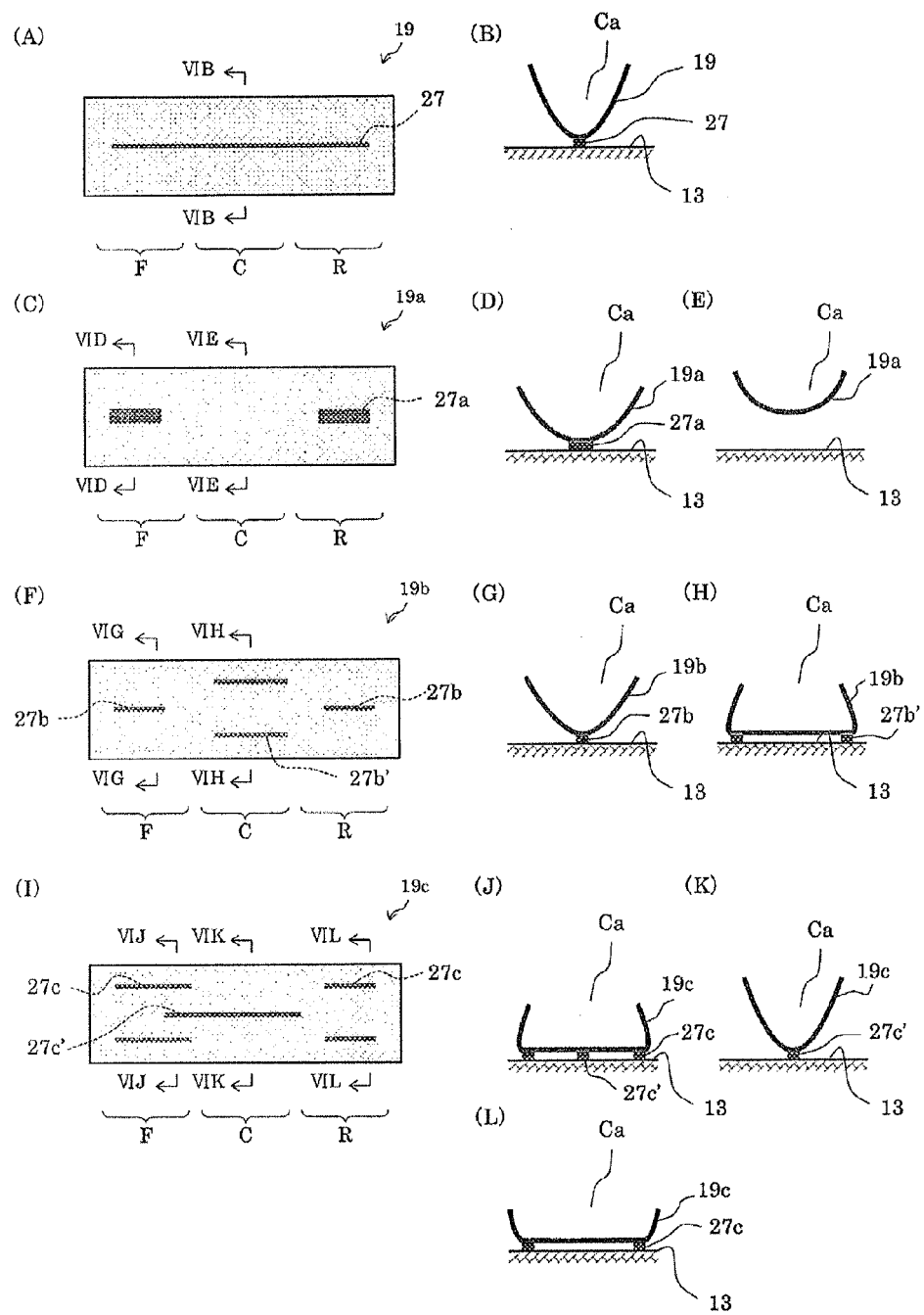

FIG. 6 contains schematic diagrams illustrating various states of formation and arrangements of the bodily fluid reception canal. FIG. 6 only shows the connection sheet and the absorber, and other members are omitted.

FIG. 6(A) is a plan view illustrating an example of the connection sheet that forms the bodily fluid reception canal. FIG. 6(B) is a lateral end view along line VIB-VIB in FIG. 6(A).

Connection sheet 19 shown in FIGS. 6(A) and 6(B) is coupled and fixed to the surface of absorber 13 by coupling part 27 that linearly extends in the front-rear direction in the center of the width direction of connection sheet 19.

Connection sheet 19 forms V-shaped bodily fluid reception canal Ca in the area from front body F to rear body R via crotch part C. More specifically, connection sheet 19 assumes the shape shown in FIG. 4(C) in the area where coupling part 27 is present, while it assumes the shape shown in FIG. 4(A) in the front end part and the rear end part where coupling part 27 is not present. Accordingly, connection sheet 19 forms a bodily fluid reception canal Ca in which two shapes lie in series with each other.

In the bodily fluid reception canal in this form, a deep formation can easily be obtained and the barrier effect can be enhanced, and the production thereof is also simple.

FIG. 6(C) is a plan view illustrating another example of the connection sheet that forms the bodily fluid reception canal. FIG. 6(D) is a lateral end view along line VID-VID in FIG. 6(C). FIG. 6(E) is a lateral end view along line VIE-VIE in FIG. 6(C).

Connection sheet 19a shown in FIGS. 6(C) to 6(E) is coupled and fixed to the surface of absorber 13 by coupling parts 27a, each of which extends in the front-rear direction in a belt-form in the center of the width direction of front body F and rear body R, and is not coupled to the surface of absorber 13 in crotch part C.

Connection sheet 19a forms V-shaped bodily fluid reception canal Ca in each of front body F and rear body R as shown in FIG. 6(D). In crotch part C, bodily fluid reception canal Ca floats from the surface of absorber 13, as shown in FIG. 6(E), and the depth thereof is small. More specifically, connection sheet 19a forms bodily fluid reception canal Ca that consists of three parts.

In the bodily fluid reception canal in this form, since transferring of bodily fluids is likely to occur in crotch part C, the amount of bodily fluid transfer to the front part and the rear part can therefore be increased.

FIG. 6(F) is a plan view illustrating a further example of the connection sheet that forms the bodily fluid reception canal. FIG. 6(G) is a lateral end view along line VIG-VIG in FIG. 6(F). FIG. 6(H) is a lateral end view along line VIH-VIH in FIG. 6(F).

Connection sheet 19b shown in FIGS. 6(F) to 6(H) is coupled and fixed to the surface of absorber 13 by coupling parts 27b, each of which linearly extends in the front-rear direction in the center of the width direction in front body F and rear body R, and is also coupled and fixed to the surface of absorber 13 by coupling parts 27b' linearly extending on the right and left sides of the connection sheet in crotch part C.

Connection sheet 19b forms V-shaped bodily fluid reception canal Ca in each of front body F and rear body R as shown in FIG. 6(G). In crotch part C, bodily fluid reception canal Ca assumes a wide-based U-shape as shown in FIG. 6(H). More specifically, connection sheet 19b forms bodily fluid reception canal Ca that consists of three parts.

The bodily fluid reception canal in this form provides an effect of relatively expanding the upper opening in the front part, which is a part where the urine excretory organ is located at the time of wearing.

FIG. 6(I) is a plan view illustrating a further example of the connection sheet that forms the bodily fluid reception canal. FIG. 6(J) is a lateral end view along line VIJ-VIJ in FIG. 6(I). FIG. 6(K) is a lateral end view along line VIK-VIK in FIG. 6(I). FIG. 6(L) is a lateral end view along line VIL-VIL in FIG. 6(I).

Connection sheet 19c shown in FIGS. 6(I) to 6(L) is fixed and coupled to the surface of absorber 13 by coupling parts 27c linearly extending on the right and left sides of the connection sheet in front body F and rear body R, and is also coupled and fixed to the surface of absorber 13 by coupling part 27c' linearly extending in the front-rear direction in the center of the width direction from crotch part C to the vicinity of the rear part of front body F.

Connection sheet 19c is coupled to the surface of absorber 13 at three locations on the under surface thereof, as shown in FIG. 6(J), and forms wide-based U-shaped bodily fluid reception canal Ca in the vicinity of the rear part of front body F. In crotch part C, bodily fluid reception canal Ca assumes a V-shape as shown in FIG. 6(K) and in each of rear body R and parts other than the vicinity of the rear part of front body F, bodily fluid reception canal Ca assumes a U-shape as shown in FIG. 6(L). More specifically, connection sheet 19c forms bodily fluid reception canal Ca that consists of four parts.

The bodily fluid reception canal in this form provides an effect of relatively expanding each of the upper opening in the front part, which is a part where the urine excretory organ is located at the time of wearing, and the upper opening in the rear part, which is a part where the feces excretory organ (the anus) is located at the time of wearing.

It should be noted that, as described above, FIG. 6 shows schematic diagrams and thus, the bodily fluid reception canal in the actual absorbent article may be easily deformed by the influence of stress or the like due to the position of existence in the front-rear direction, the degree of stretchability of the belt-like supporters, etc., even when the positions of the coupling parts between the bottom surface of the connection sheet and the absorber surface are identical.

For example, when the connection structure receives stress in the front-rear direction, the belt-like supporters in a contracted state extend in the front-rear direction, and this will expand the opening (i.e. the space between the pair of right and left belt-like supporters) of the bodily fluid reception canal in the lateral direction. In the case of the V-shaped form, a widely-opened shape is obtained. In contrast, when the connection structure does not receive stress in the front-rear direction, the opening (i.e. the space between the pair of right and left belt-like supporters) of the bodily fluid reception canal narrows down in the lateral direction due to the belt-like supporters in the contracted state. In the case of the V-shaped form, a narrowly-closed shape is obtained.

Bodily fluid reception canal Ca provides a function of allowing the reception of the bodily fluids excreted from the wearer and the transfer thereof to the absorber; however, the configuration thereof is not particularly limited.

First, examples are provided of the form in which a connection sheet is used, the entirety thereof being liquid permeable. More specifically, examples are provided including: a form in which the connection sheet is configured by a hydrophilic material (for example, a cellulosic non-woven fabric) (for example, connection sheet 18 in above-described absorbent article 100); a form in which the connection sheet is configured by a hydrophobic non-woven fabric (for example, a spunmelt non-woven fabric) being provided with liquid permeability through hydrophilization treatment; and a form in which the connection sheet is configured by a material physically provided with liquid permeability (for example, a liquid permeable apertured film such as an apertured PE film).

Second, examples are provided of the form in which a connection sheet is used, a part thereof being liquid permeable. More specifically, examples are provided including: a form in which a part of the connection sheet (for example, the part configuring the bottom surface of the connection sheet or the part corresponding to the crotch part of the wearer) is configured by a hydrophilic material (for example, a cellulosic non-woven fabric); and a form in which a part of the connection sheet (for example, the part configuring the bottom surface of the connection sheet or the part corresponding to the crotch part of the wearer) is configured by a hydrophobic non-woven fabric (for example, a spunmelt non-woven fabric) being provided with liquid permeability through hydrophilization treatment.

Third, examples are provided of the form in which a connection sheet is used, which is provided with an exit for allowing transfer of bodily fluids. Examples of exits for allowing the transfer of bodily fluids include: a notch, an opening and a slit. Each of them may be used alone or two or more types may be used together.

The shape, size, position, number or the like of the notch is not limited.

The shape, size, position, number or the like of the opening is not limited. Examples of the shape of the opening include a circle, a triangle, a square, a star shape and an irregular shape. These may be used in appropriate combinations.

It should be noted that, in the present invention, although the notch and the opening are essentially the same, an exit with a relatively large size will be referred to as a notch and an exit with a relatively small size will be referred to as an opening (i.e. a plurality of such exits are preferably provided at one location).

The shape, size, position, number or the like of the slit is not limited. Examples of the shape of the slit include a linear form, an arc form and a C-shaped curved form. Examples of the position of the slit include the width direction, the diagonal direction and the front-rear direction. These may be used in appropriate combinations.

FIG. 7 contains schematic plan views illustrating examples of the connection sheet provided with various notches.

In connection sheet 19d shown in FIG. 7(A), one large notch 34 is provided from front body F to rear body R.

In connection sheet 19e shown in FIG. 7(B), notch 34a in a substantially rectangular shape is provided in front body F and notch 34b in a substantially rectangular shape is provided from the vicinity of the rear end of crotch part C to rear body R. When providing two or more notches, as in this case, the shape or size may be the same or different. In connection sheet 19e, the shape and the size of notch 34a and notch 34b are different.

FIG. 8 contains schematic plan views illustrating examples of the connection sheet provided with various openings.

In connection sheet 19f shown in FIG. 8(A), a plurality of openings 36 having the same shape (here, circular) and size are provided. A large number of openings are arranged in front body F and rear body R, and a small number of openings are arranged in crotch part C. In this way, the bodily fluids received by the bodily fluid reception canal mainly transfer from front body F and rear body R to the absorber.

In connection sheet 19g shown in FIG. 8(B), a plurality of openings 36a having the same shape (here, circular) but different sizes are provided. Large openings are arranged in front body F and rear body R, and small openings are arranged in crotch part C. In this way, the bodily fluids received by the bodily fluid reception canal mainly transfer from front body F and rear body R to the absorber.

In connection sheet 19h shown in FIG. 8(C), a plurality of openings 36b having the same shape (here, circular) but different sizes are provided. A few large openings and a plurality of small openings are arranged in front body F and rear body R, and a small number of small openings are provided in crotch part C. In this way, the bodily fluids received by the bodily fluid reception canal mainly transfer from front body F and rear body R to the absorber.

FIG. 9 contains schematic plan views illustrating examples of the connection sheet provided with various slits.

In connection sheet 19i shown in FIG. 9(A), linear slit 38 extending in the front-rear direction is provided, in the center in the lateral direction, in the region from the vicinity of the rear end of crotch part C to rear body R.

In connection sheet 19j shown in FIG. 9(B), one C-shaped curved slit 38a extending in the lateral direction is provided in each of front body F and rear body R.

In connection sheet 19k shown in FIG. 9(C), one C-shaped curved slit 38b extending in the lateral direction is provided in each of front body F and rear body R, and one C-shaped curved slit 38b extending in the lateral direction is provided in each of the vicinity of front body F and the vicinity of rear body R front body F in crotch part C. The plurality of slits 38b have different sizes.

In connection sheet 19l shown in FIG. 9(D), a plurality of linear slits 38c extending in the lateral direction are provided in front body F, and a plurality of linear slits 38c extending in the lateral direction are provided in the region from crotch part C to rear body R. The plurality of slits 38c have different sizes.

In connection sheet 19m shown in FIG. 9(E), a plurality of linear slits 38d extending in the front-rear direction are provided in front body F, and a plurality of linear slits 38d extending in the front-rear direction are provided in the region from crotch part C to rear body R. The plurality of slits 38d have different sizes.

In connection sheet 19n shown in FIG. 9(F), a plurality of linear slits 38e extending in the front-rear direction and C-shaped curved slit 38e extending in the lateral direction are provided in front body F, and a plurality of linear slits 38e extending in the front-rear direction are provided in the region from crotch part C to rear body R. The plurality of slits 38e have different sizes.

FIG. 10 contains schematic plan views illustrating examples of the connection sheet provided with various exits.

In connection sheet 19o shown in FIG. 10(A), C-shaped curved slit 38f extending in the lateral direction is provided in front body F, linear slit 38f extending in the front-rear direction is provided, in center of the lateral direction, in the region from the vicinity of the rear end of front body F to the vicinity of the front end of crotch part C, and substantially rectangular notch 34c is provided in the region from the vicinity of the rear end of crotch part C to rear body R.

In connection sheet 19p shown in FIG. 10(B), crescent notch 34d is provided in each of front body F and rear body R, and multiple openings 36c having the same shape (here, circular) and size are provided in each of the region from front body F to crotch part C and the region from crotch part C to rear body R.

As described above, it is preferable to provide at least one exit selected from the group consisting of a notch, an opening and a slit in the connection sheet part that forms the bodily fluid reception canal. Accordingly, the bodily fluids can be discharged in a concentrated manner from a specific part of the bodily fluid reception canal. In one of the preferred embodiments, even when the connection sheet is configured by a liquid permeable material, at least one exit selected from the group consisting of a notch, an opening and a slit is still provided.

As in connection sheet 18 in above-described absorbent article 100, even when at least one exit selected from the group consisting of a notch, an opening and a slit is not provided, a relatively wide range of the absorber can be utilized; however, the effect thereof will be more significant when such exit is provided.

For example, even when the prone position is maintained, wherein urine tends to concentrate in a part of the absorber present in the front body, even when the supine position is maintained, wherein urine tends to concentrate, by passing the crotch part, in a part of the absorber present in the rear body, and even when the recumbent position is maintained, wherein urine tends to concentrate in either the right or the left of the absorber, urine does not get absorbed into the crotch part, in a concentrated manner, and can be made to be absorbed efficiently by the absorber across the entirety of the front body and the rear body.

In particular, when the bodily fluids can be distributed evenly to the right and to the left in the front body and the rear body of the absorber at the beginning of bodily fluid absorption while avoiding the crotch part, the entire area of the absorber can be utilized up to the absorption capacity limit possessed by the absorber.

Subsequently, the belt-like supporters will be described.

The belt-like supporter preferably has stretchability in at least part thereof. This is because it is preferable that the upper side surface of the belt-like supporter is in constant contact with the wearer's skin and that it is constantly fitted thereto without a gap even when the wearer conducts various movements.

In particular, it is preferable for the belt-like supporter to be configured using a stretchable elastic material. This allows the belt-like supporter to provide stretchability and cushioning properties, to be provided with irregularities, and to be able to enhance fitting properties with respect to the wearer's skin through elasticity.

An example of the stretchable elastic material includes a material used as a gather material in the absorbent article such as conventional diapers. In particular, a polyurethane filament, yarn-like rubber, a synthetic rubber film or a stretchable foam sheet may be used.

The belt-like supporter is preferably obtained by covering the above-described stretchable elastic material with a non-woven fabric.

Such non-woven fabric preferably has a soft and smooth surface and provides less irritation to the skin. For example, a dry non-woven fabric or a spunmelt non-woven fabric configured mainly by synthetic fiber such as PE fiber, PP fiber, PET fiber, PE/PP composite fiber, PE/PET composite fiber or the like is preferred. The fineness of the fiber used in the non-woven fabric is preferably relatively small, and in particular, 5 deniers or less is preferred. Preferably, the basis weight of the non-woven fabric is relatively small, and in particular, a basis weight of 5 to 30 g/m$^2$ is preferred.

Figure 11:
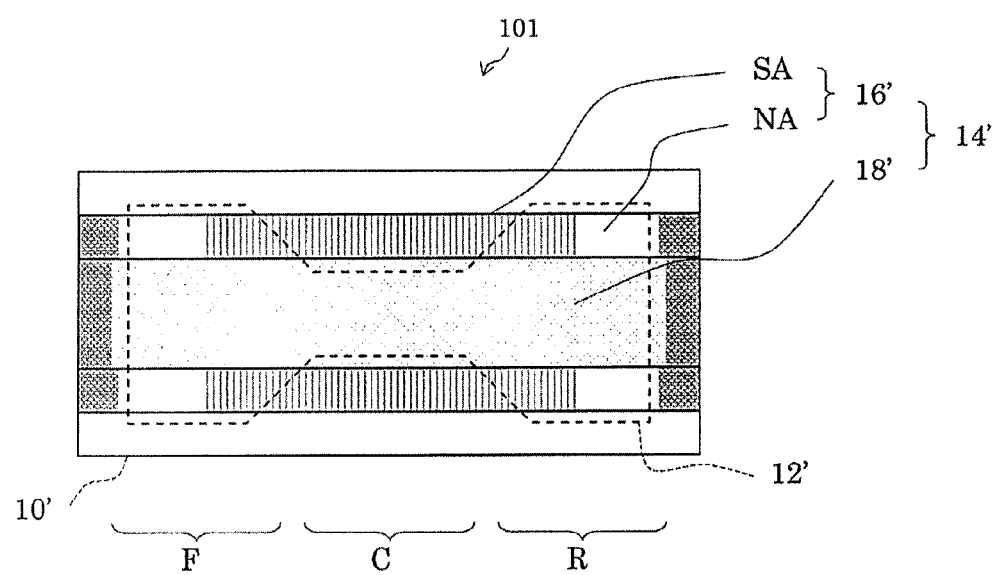

FIG. 11 is a schematic diagram illustrating an example of a state of arrangement of the belt-like supporters in the absorbent article.

Absorbent article 101 shown in FIG. 11 is a simplified version of absorbent article 100 shown in FIG. 1 in order to describe the state of arrangement of the belt-like supporters. Leak preventer 10', absorber 12', connection structure 14', belt-like supporters 16' and connection sheet 18' are respectively similar to leak preventer 10, absorber 12, connection structure 14, belt-like supporters 16 and connection sheet 18.

Belt-like supporter 16' includes stretchable area SA, which is present from the center of front body F to the center of rear body R, and non-stretchable areas NA, which are present forward of the center of front body F and rearward of the center in rear body R.

In stretchable area SA, belt-like supporter 16' is configured by the stretchable material and a non-woven fabric that covers the same. In non-stretchable areas NA, belt-like supporter 16' is configured by a non-woven fabric (see FIG. 1).

Figure 12:
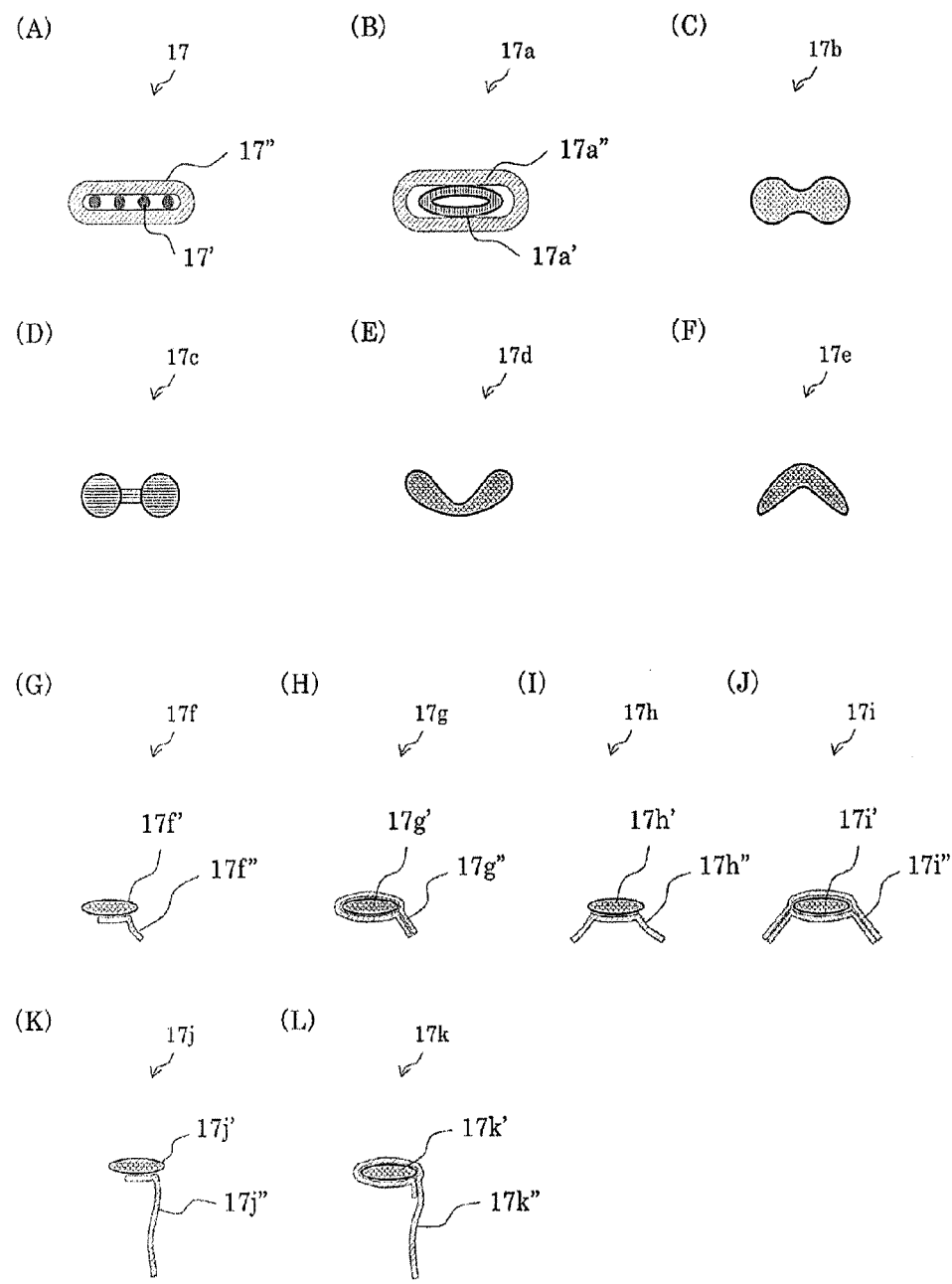

FIG. 12 contains schematic lateral end views illustrating examples of various belt-like supporters. FIGS. 12(C) to 12(F) only show the stretchable material and others are omitted.

Belt-like supporter 17 shown in FIG. 12(A) is configured by arranging four stretchable elastic materials 17' and covering the same, from the above and the bottom, with non-woven fabric 17". As for stretchable elastic material 17', for example, a urethane filament (for example, 400 dtex) may be used. As for non-woven fabric 17", for example, a PE/PP non-woven fabric (having, for example, a basis weight of 12 g/m$^2$ and which is manufactured by Chisso Corporation) may be used. The width in the lateral direction of belt-like supporter 17 can be set to be approximately 15 mm.

Belt-like supporter 17a shown in FIG. 12(B) is configured by covering the top and the bottom of tube-shaped stretchable elastic material 17a' with non-woven fabric 17a". As for stretchable elastic material 17a', for example, a thin-walled rubber tube (for example, with a lateral width of 10 mm) may be used. As for non-woven fabric 17", for example, a PE/PP non-woven fabric (having, for example, a basis weight of 12 g/m$^2$ and which is manufactured by Chisso Corporation) may be used.

Belt-like supporter 17b shown in FIG. 12(C) is configured by a cocoon-shaped stretchable elastic material.

Belt-like supporter 17c shown in FIG. 12(D) is configured by a dumbbell-shaped stretchable elastic material.

Belt-like supporter 17d shown in FIG. 12(E) is configured by a V-shaped stretchable elastic material.

Belt-like supporter 17e shown in FIG. 12(F) is configured by a reverse V-shaped stretchable elastic material.

An example of the stretchable elastic material used in belt-like supporters 17b, 17c, 17d and 17e includes polyether-based polyurethane foam with a large stretchability.

In belt-like supporter 17f shown in FIG. 12(G), non-woven fabric 17f" couples to the under surface of stretchable elastic material 17f' and non-woven fabric 17f" hangs down from one side of stretchable elastic material 17f' in fringe form.

In belt-like supporter 17g shown in FIG. 12(H), non-woven fabric 17g" covers stretchable elastic material 17g' and non-woven fabric 17" hangs down from one side of stretchable elastic material 17g' in fringe form.

In belt-like supporter 17h shown in FIG. 12(I), non-woven fabric 17h" couples to the under surface of stretchable elastic material 17h' and non-woven fabric 17h" hangs down from both sides of stretchable elastic material 17h' in fringe form.

In belt-like supporter 17i shown in FIG. 12(J), non-woven fabric 17i" covers stretchable elastic material 17i' and non-woven fabric 17i" hangs down from both sides of stretchable elastic material 17i' in fringe form.

In belt-like supporter 17j shown in FIG. 12(K), non-woven fabric 17j" couples to the under surface of stretchable elastic material 17F and non-woven fabric 17j" hangs down from one side of stretchable elastic material 17F in curtain form.

In belt-like supporter 17k shown in FIG. 12(L), non-woven fabric 17k" covers stretchable elastic material 17k' and non-woven fabric 17k" hangs down from one side of stretchable elastic material 17k' in curtain form.

As described above, when a belt-like supporter has a part hanging down in fringe or curtain form, the coupling with respect to the connection sheet becomes strong and is simplified.

Hereinafter, more specific embodiments of the absorbent article according to the present invention will be described; however, prior to this, a conventional absorbent article to be compared thereto will be described.

FIG. 17 contains schematic diagrams illustrating an example of the conventional absorbent article. FIG. 17(A) is a developed plan view which schematically shows the state in which an absorbent article, in the form of an underpants-type diaper for adults ("Atento," a super-slim underpants-type diaper (size LL) manufactured by Daio Paper Corporation), is cut along the right and left side parts (denoted with Z and Z' in the figure) of the waist gather and in which stress is applied to the absorbent article such that it is pulled in the front-rear direction and the lateral direction so as to be developed into a substantially planar form. FIG. 17(B) is a lateral end view along line XVIIB-XVIIB in FIG. 17(A). FIG. 17(C) is a lateral end view along line XVIIC-XVIIC in FIG. 17(A) of the case when stress is not applied to the absorbent article (i.e. in a relaxed state).

Absorbent article 200 shown in FIG. 17 is a representative article of an underpants-type diaper for adults. The length in the front-rear direction of absorbent article 200 is 850 mm and the width in the lateral direction thereof is 700 mm.

Absorbent article 200 is provided with, from the bottom, external covering sheet 40, leak preventer 10a, absorber 12a and top sheet 32a that covers the upper surface of absorber 12a, and is configured by further including waist gathers 42, shirring gathers 44 and stereoscopic leg gathers (SLGs) 46, which are the gather components.

External covering sheet 40 is a member that is used in an underpants-type diaper and that bears a fitting function of enfolding the wearer's body. Specifically, a sheet-form member forming the respective parts of front body F, crotch part C and rear body R is used.

In an underpants-type diaper such as absorbent article 200, since the leak preventer prevents the leakage of urine or the like, it is unnecessary to use liquid impermeable materials for the external covering sheet. For example, for the external covering sheet, any external covering sheet that is used in publicly-known conventional absorbent articles may be used. In particular, a non-woven fabric configured by synthetic fibers made of, for example, polyethylene, polypropylene, polyester, or other thermoplastic resin may be used as the external covering sheet.

In absorbent article 200, external covering sheet 40 is configured by a spunbond non-woven fabric made of PP fiber (having a basis weight of 17 g/m$^2$).

Leak preventer (back sheet) 10a is configured by an air permeable film made of PE resin (having a basis weight of 20 g/m²).

Absorber 12a has a configuration in which the mixture mat of SAP and pulp is wrapped by a crepe paper, wherein the SAP content is 9 g/sheet, the pulp content is 11 g/sheet and the crepe paper has a basis weight of 18 g/m².

Top sheet 32a is configured by a liquid permeable air-through non-woven fabric (having a basis weight of 21 g/m²), which has PE/PET fiber (1.5 d×45 mm) as a primary component thereof.

The waist gather serves as a fixing band that connects the front end part of the absorbent article body to the rear end part thereof, attaches the diaper closely around the waist and prevents the absorbent article from sliding down.

In absorbent article 200, waist gather 42 is configured by arranging five natural rubber yarns (1.0 mm×0.35 mm) in a stretched state of approximately 260%, by sandwiching the same with top and bottom spunbond non-woven fabrics, and by joining the same to these spunbond non-woven fabrics.

The shirring gathers are provided at positions where they cover the abdominal area and the back area of the wearer at the time of wearing.

In absorbent article 200, shining gather 44 is configured by arranging a total of twenty filaments, more specifically, five polyurethane filaments (spandex 620 dtex) in a stretched state of approximately 200% and fifteen polyurethane filaments with spandex 310 dtex in a stretched state of approximately 250%, by sandwiching them with upper and lower spunbond non-woven fabrics, and by joining them to the spunbond non-woven fabrics.

Stereoscopic leg gather (SLG) 46 is configured by arranging four polyurethane filaments (spandex 620 dtex) in a stretched state of approximately 270%, by sandwiching them with top and bottom spunbond non-woven fabrics, and by joining them to the spunbond non-woven fabrics. Stereoscopic leg gather (SLG) 46 is arranged on the right and left side edges.

The absorption capacity of absorbent article 200 was approximately 680 g per piece, when it was determined by a method including: immersing absorbent article 200 in saline to let it absorb the same; dehydrating it under a weight of 1.4 kg/100 cm²; and subtracting the weight prior to absorption to measure the absorption amount after dehydration.

Next, a more specific embodiment of the absorbent article according to the present invention will now be described.

Figure 13:
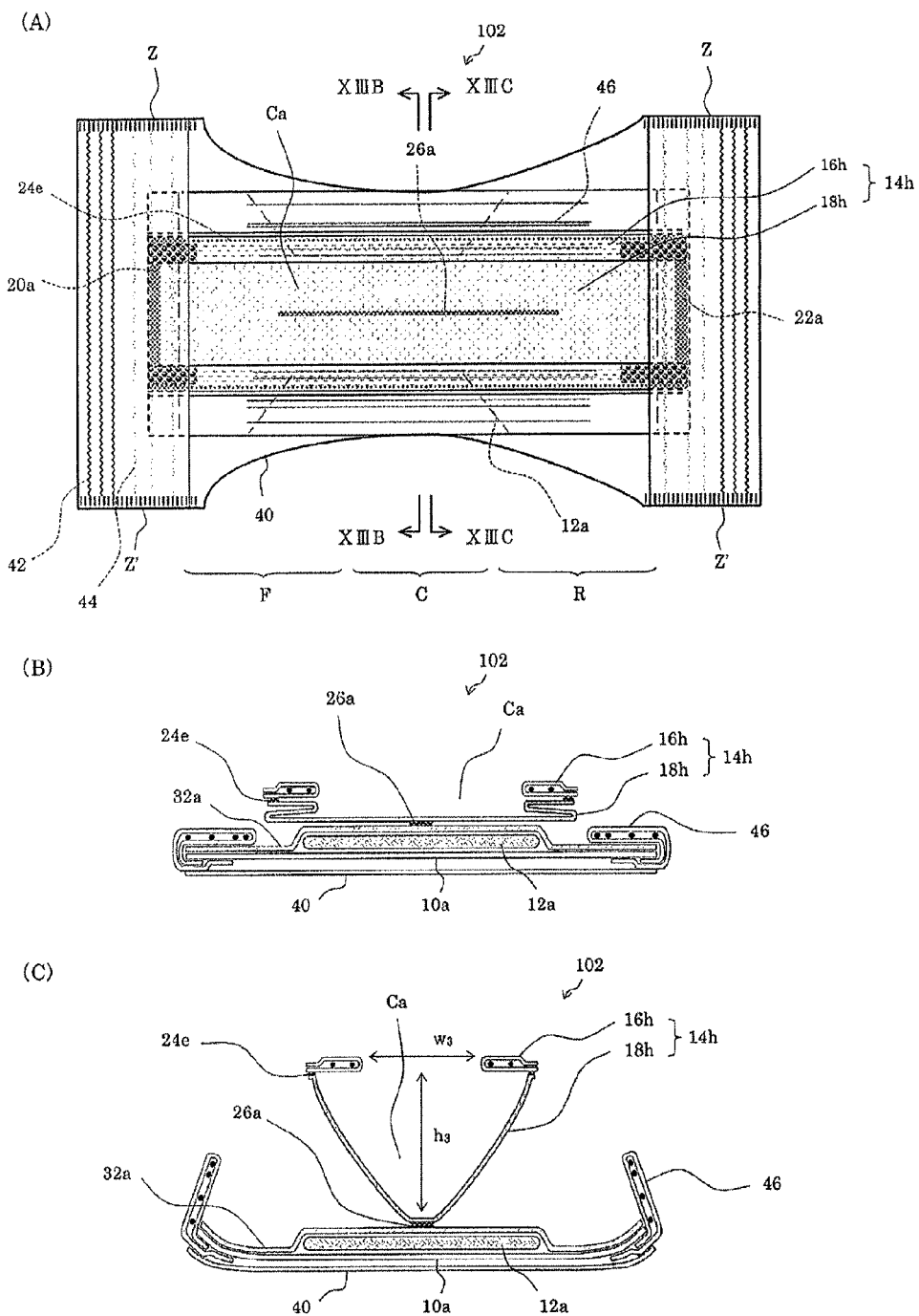

FIG. 13 contains schematic diagrams illustrating an embodiment of the absorbent article according to the present invention. FIG. 13 (A) is a developed plan view which schematically shows the state in which an absorbent article, in the form of an underpants-type diaper, is cut along the right and left side parts (denoted with Z and Z' in the figure) of the waist gather and in which stress is applied to the absorbent article such that it is pulled in the front-rear direction and the lateral direction so as to be developed into a substantially planar form. FIG. 13(B) is a lateral end view along line XIIIB-XIIIB in FIG. 13(A). FIG. 13(C) is a lateral end view along line XIIIC-XIIIC in FIG. 13(A) of the case when stress is not applied to the absorbent article (i.e. in a relaxed state).

Absorbent article 102 shown in FIG. 13 is configured as an underpants-type diaper for adults. Absorbent article 102 corresponds to absorbent article 200 shown in FIG. 17 having connection structure 14h that forms bodily fluid reception canal Ca incorporated therein. More specifically, absorbent article 102 is obtained by respectively coupling and integrating a front end and a rear end of connection structure 14h to/in absorbent article 200 at front end coupling part 20a and rear end coupling part 22a, and then by further coupling connection sheet 18h of connection structure 14h to the surface of top sheet 32a at coupling part 26a.

In absorbent article 102, connection structure 14h forms V-shaped bodily fluid reception canal Ca. The degree of hanging ($h_3/w_3$) of the bodily fluid reception canal is approximately 2.0 in crotch part C. In a relaxed state, bodily fluid reception canal Ca is formed and the SLGs stand up in absorbent article 102 (see FIG. 13 (C)).

FIG. 14 contains schematic diagrams illustrating connection structure 14h. FIG. 14(A) is a plan view and FIG. 14(B) is a lateral end view along line XIVB-XIVB in FIG. 14(A).

Connection structure 14h includes a pair of right and left belt-like supporters 16h and connection sheet 18h, the right and left edge parts thereof respectively coupling to the pair of right and left belt-like supporters 16h. The upper surfaces of the right and left edge parts of connection sheet 18h are coupled to the underside of the pair of right and left belt-like supporters 16h at coupling parts 24e.

Belt-like supporter 16h is configured, similar to belt-like supporter 17h shown in FIG. 12(A), by arranging two stretchable elastic materials (made of spandex with 310 dtex) and by covering the same from the top and the bottom with non-woven fabrics. In addition, similar to belt-like supporter 17g shown in FIG. 12(H), the non-woven fabric of belt-like supporter 16h hangs down from one side of the stretchable elastic material in fringe form. The width in the lateral direction of belt-like supporter 16h is 20 mm.

Connection sheet 18h is made to have a width of 120 mm by folding both side edges, by 20 mm, of a liquid permeable hydrophilic air-through non-woven fabric (made of PE/PET and having a basis weight of 20 g/m²) having a length in the front-rear direction of 550 mm and a width in the lateral direction of 200 mm.

The fringe parts of the non-woven fabric of belt-like supporters 16h and both side edges of connection sheet 18h are joined together by a hot melt adhesive.

In the range from a part of front body F to a part in rear body R via crotch part C, the under surface of connection sheet 18h of connection structure 14h, in the vicinity of the center in the lateral direction of connection sheet 18h, is coupled to the surface of top sheet 32a at coupling parts 26a by means of a linearly-provided hot melt adhesive.

Absorbent article 102 has bodily fluid reception canal Ca from the front end to the rear end thereof, in a continuous manner, and a lateral end section thereof is shown in FIG. 13(C).

Although an exit for bodily fluids such as a notch is not provided to bodily fluid reception canal Ca, since connection sheet 18h is a liquid permeable non-woven fabric, the transfer and distribution of bodily fluids to/over the surface of absorber 12a are performed through fine pores provided across the entirety of connection sheet 18h.

When urine is excreted at the time of wearing absorbent article 102, the total amount of the excreted urine is received in bodily fluid reception canal Ca. The received urine is distributed and discharged from fine pores of connection sheet 18h onto the surface of absorber 12a, as it transfers to the front and to the rear within bodily fluid reception canal Ca.

As a result, the amount of urine excreted onto the part of absorber 12a which is present in the crotch part is significantly reduced and thus, leakage of urine from the side surfaces of the crotch part is almost certainly prevented.

On the other hand, the amount of urine supplied to the parts present in the front part and the rear part of absorber 12a is increased.

When feces are excreted at the time of wearing absorbent article 102, the total amount of the excreted feces is received in bodily fluid reception canal Ca. The liquid components within the feces are discharged from fine pores in connection sheet 18h, similar to urine, whereby the condensed solid components stay within bodily fluid reception canal Ca as is, and thus, urine-feces separation is naturally performed. The feces transfer, depending on the amount thereof, in the direction of the front part within bodily fluid reception canal Ca and thus, spreading to the exterior of bodily fluid reception canal Ca is prevented.

As a general rule, when feces are excreted, changing of the diaper is performed. However, out of all of the wearer's skin, the region that becomes dirty due to the feces is limited to the periphery of the anus, and thus, cleaning operations by care-takers can be performed more easily. In addition, for the reason stated above, the removal of diapers also becomes easy and thus, the time and effort needed for disposal are reduced.

Figure 15:
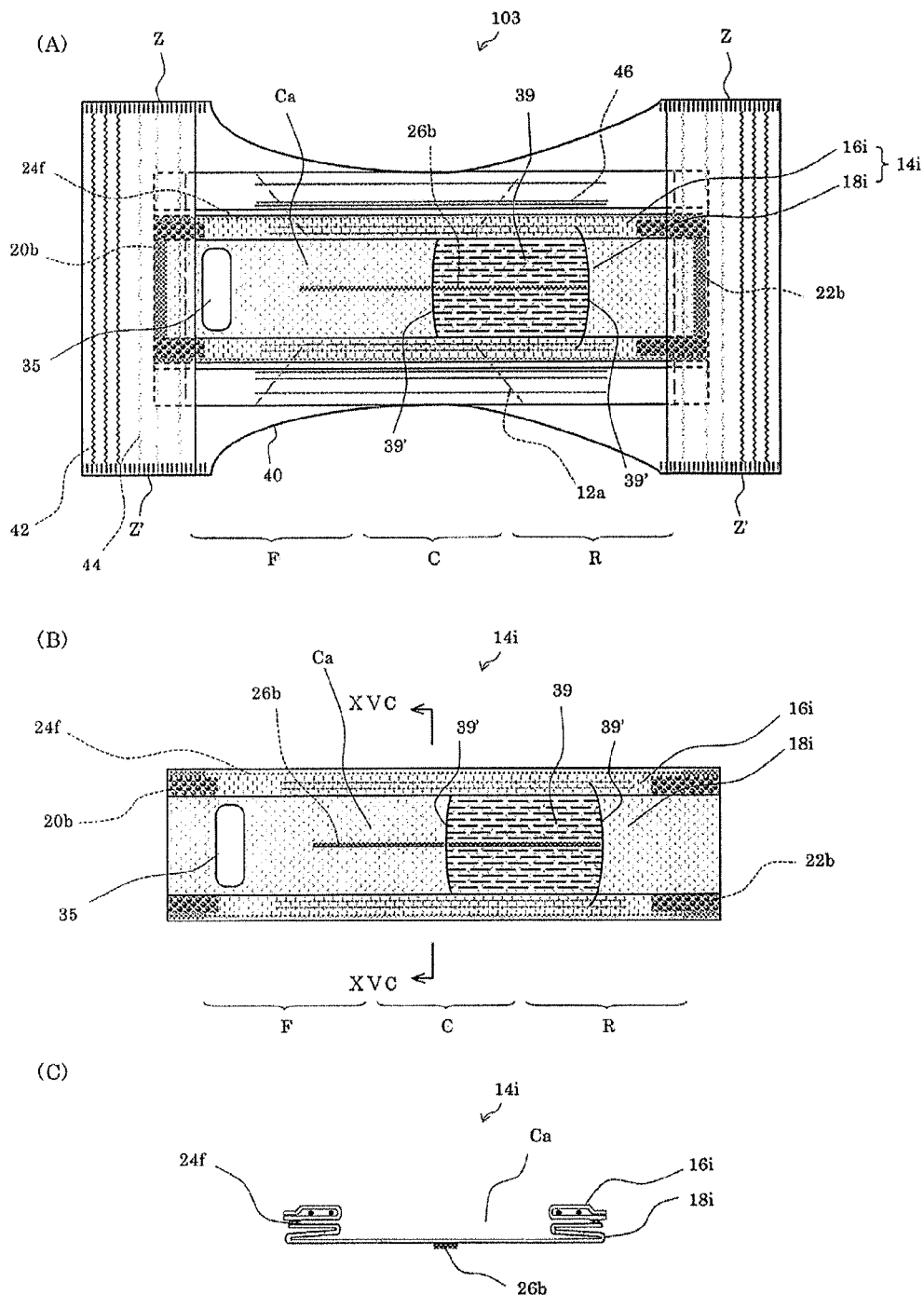

FIG. 15 contains schematic diagrams illustrating another embodiment of the absorbent article according to the present invention. FIG. 15 (A) is a developed plan view which schematically shows the state in which an absorbent article, in the form of an underpants-type diaper, is cut along the right and left side parts (denoted with Z and Z' in the figure) of the waist gather and in which stress is applied to the absorbent article such that it is pulled in the front-rear direction and the lateral direction so as to be developed into a substantially planar form. FIG. 15(B) is a schematic plan view illustrating a connection structure used in the absorbent article shown in FIG. 15(A). FIG. 15(C) is a lateral end view along line XVC-XVC in FIG. 15(B).

Absorbent article 103 shown in FIG. 15 is configured as an underpants-type diaper for adults. Absorbent article 103 corresponds to absorbent article 200 shown in FIG. 17 having connection structure 14i that forms bodily fluid reception canal Ca incorporated therein. More specifically, absorbent article 103 is obtained by respectively coupling and integrating the front end and the rear end of connection structure 14i to/in absorbent article 200 at front end coupling part 20b and rear end coupling part 22b and then by further coupling connection sheet 18i of connection structure 14i to the surface of top sheet 32a at coupling part 26b.

Connection structure 14i includes a pair of right and left belt-like supporters 16i and connection sheet 18i, the right and left edge parts thereof respectively coupling to the pair of right and left belt-like supporters 16i. The upper surfaces of the right and left edge parts of connection sheet 18i are coupled to the underside of the pair of right and left belt-like supporters 16i at coupling parts 24f.

Belt-like supporter 16i is configured, similar to belt-like supporter 17 shown in FIG. 12(A), by arranging two stretchable elastic materials (made of spandex with 310 dtex) and by covering the same from the top and the bottom with non-woven fabrics. In addition, similar to belt-like supporter 17g shown in FIG. 12(H), the non-woven fabric of belt-like supporter 16i hangs down from one side of the stretchable elastic material in fringe form. The width in the lateral direction of belt-like supporter 16i is 20 mm.

Connection sheet 18i is made to have a width of 120 mm by folding both side edges, by 20 mm, of a hydrophobic spunmelt non-woven fabric (a PP-based SMS non-woven fabric having a basis weight of 15 g/m$^2$) having a length in the front-rear direction of 550 mm and a width in the lateral direction of 200 mm. Further, a small notch 35 in a rectangular shape with rounded corners is provided in the vicinity of the front end of front body F, a plurality of fine slits 39 extending in the front-rear direction are provided in the area from crotch part C to rear body R, and lateral C-shaped slits 39' extending in the lateral direction are respectively provided on the front end and the rear end of slits 39, and the notch, fine slits and C-shaped slits are respectively provided as an exit for bodily fluids.

The fringe parts of the non-woven fabric of belt-like supporters 16i and both side edges of connection sheet 18i are joined together by a hot melt adhesive.

In the range from a part in front body F to a part in rear body R via crotch part C, the under surface of connection sheet 18i of connection structure 14i, in the vicinity of the center in the lateral direction connection sheet 18i, is coupled to the surface of top sheet 32a at coupling parts 26a by means of a linearly-provided hot melt adhesive.

Absorbent article 103 has bodily fluid reception canal Ca from the front end to the rear end thereof, in a continuous manner, which has a lateral end section similar to that shown in FIG. 13(C).

In bodily fluid reception canal Ca, the transfer and distribution of bodily fluids to/over the surface of absorber 12a are performed only through notch 35, slits 39 and slits 39'.

When urine is excreted at the time of wearing absorbent article 103, the total amount of the excreted urine is received in bodily fluid reception canal Ca. The received urine is distributed and discharged from notch 35, slits 39 and slits 39' onto the surface of absorber 12a, as it transfers to the front and to the rear within bodily fluid reception canal Ca.

Since connection structure 14i does not have an exit for bodily fluids in the crotch part, as a result thereof, urine is not directly discharged onto the part of the absorber which is present in the crotch part and thus, leakage of urine from the side surfaces of the crotch part is almost certainly prevented.

On the other hand, the amount of urine supplied to the parts present in the front part and the rear part of absorber 12a is increased as compared to that in absorbent article 102 shown in FIG. 13.

When feces are excreted at the time of wearing absorbent article 103, the total amount of the excreted feces is received in bodily fluid reception canal Ca. The liquid components within the feces are discharged from slits 39 and slits 39' in connection sheet 18h, similar to urine, whereby the condensed solid components stay within bodily fluid reception canal Ca as is, and thus, urine-feces separation is naturally performed. The feces transfer, depending on the amount thereof, transfer in the direction of the front part within bodily fluid reception canal Ca and thus, spreading to the exterior of bodily fluid reception canal Ca is prevented.

As a general rule, when feces are excreted, changing of the diaper is performed. However, out of all of the wearer's skin, the region that becomes dirty due to the feces is limited to the periphery of the anus, and thus, bed-bath operations by care-takers can be performed more easily. In addition, for the reason stated above, the removal of diapers also becomes easy and thus, the time and effort needed for disposal are reduced.

Figure 16:
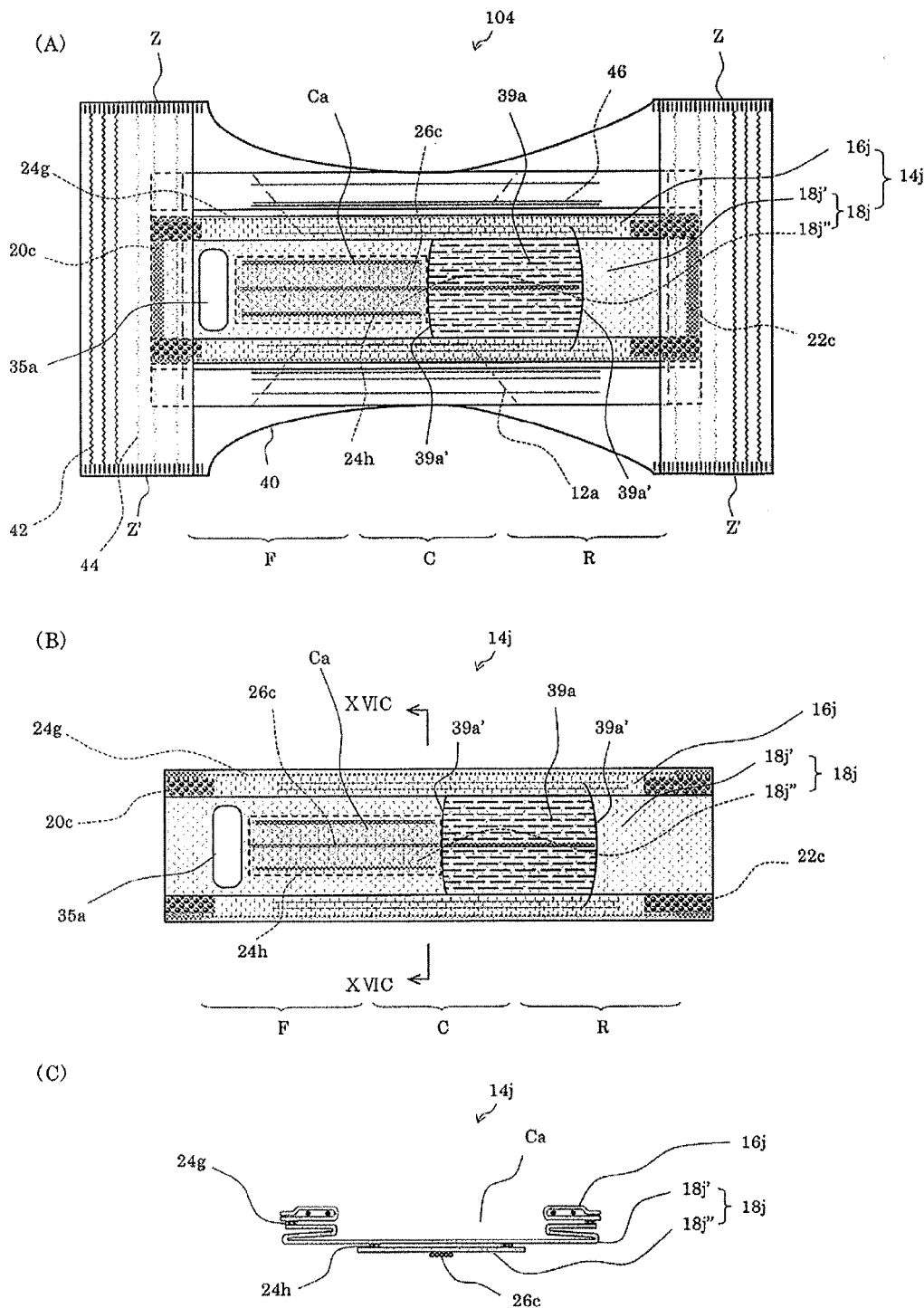

FIG. 16 contains schematic diagrams of a further embodiment of the absorbent article according to the present invention. FIG. 16 (A) is a developed plan view which schematically shows the state in which an absorbent article, in the form of an underpants-type diaper, is cut along the right and left side parts (denoted with Z and Z' in the figure) of the waist gather and in which stress is applied to the absorbent article such that it is pulled in the front-rear direction and the lateral direction so as to be developed into a substantially planar form. FIG. 16(B) is a schematic plan view illustrating a connection structure used in the absorbent article shown in FIG. 16(A). FIG. 16(C) is a lateral end view along line XVIC-XVIC in FIG. 16(B).

Absorbent article 104 shown in FIG. 16 is configured as an underpants-type diaper for adults. Absorbent article 104 corresponds to absorbent article 200 shown in FIG. 17 having connection structure 14*j* that forms bodily fluid reception canal Ca incorporated therein. More specifically, absorbent article 104 is obtained by respectively coupling and integrating a front end and a rear end of connection structure 14*j* to/in absorbent article 200 at front end coupling part 20*c* and rear end coupling part 22*c* and then by further coupling connection sheet 18*j* of connection structure 14*j* to the surface of top sheet 32*a* at coupling part 26*c*.

Connection structure 14*j* includes a pair of right and left belt-like supporters 16*j* and connection sheet 18*j*, the right and left edge parts thereof respectively coupling to the pair of right and left belt-like supporters 16*j*. The upper surfaces of the right and left edge parts of connection sheet 18*j* are coupled to the underside of the pair of right and left belt-like supporters 16*j* at coupling parts 24*g*.

Belt-like supporter 16*j* is configured, similar to belt-like supporter 17 shown in FIG. 12(A), by arranging two stretchable elastic materials (made of spandex with 310 dtex) and by covering the same from the top and the bottom with non-woven fabrics. In addition, similar to belt-like supporter 17*g* shown in FIG. 12(H), the non-woven fabric of belt-like supporter 16*j* hangs down from one side of the stretchable elastic material in fringe form. The width in the lateral direction of belt-like supporter 16*j* is 20 mm.

Connection sheet 18*i* is configured by: hydrophilic sheet 18F which is made of a hydrophilization-treated spunbond non-woven fabric (made of PE/PP and which has a basis weight of 17 g/m$^2$) having a length in the front-rear direction of 550 mm and a width in the lateral direction of 200 mm; and hydrophobic sheet 18*j*" which is made of a hydrophobic spunmelt non-woven fabric (a PP-based SMS non-woven fabric having a basis weight of 15 g/m$^2$) having a length in the front-rear direction of 200 mm and a width in the lateral direction of 70 mm. Connection sheet 18*j* forms a multilayer sheet by bonding hydrophilic sheet 18F and hydrophobic sheet 18*j*" together, similar to connection sheet 18*d* shown in FIG. 3(D), and is made to have a width of 120 mm by folding both side edges thereof by 20 mm. Further, a small notch 35*a* in a rectangular shape with rounded corners is provided in the vicinity of the front end of front body F, a plurality of fine slits 39*a* extending in the front-rear direction are provided in the area from crotch part C to rear body R, and lateral C-shaped slits 39*a*' extending in the lateral direction are respectively provided on the front end and the rear end of slits 39*a*, and the notch, fine slits and C-shaped slits are respectively provided as an exit for bodily fluids. Hydrophobic sheet 18*j*" is positioned between notch 35*a* and slit 39*a*' on the front side.

The fringe parts of the non-woven fabric of belt-like supporters 16*j* and both side edges of connection sheet 18*j* are joined together by a hot melt adhesive.

In the range from a part in front body F to a part in rear body R via crotch part C, the under surface of connection sheet 18*j* of connection structure 14*j*, in the vicinity of the center in the lateral direction of connection sheet 18*j*, is coupled to the surface of top sheet 32*a* at coupling parts 26*c* by means of a linearly-provided hot melt adhesive.

Absorbent article 104 has bodily fluid reception canal Ca from the front end to the rear end thereof, in a continuous manner, which has a lateral end section similar to that shown in FIG. 13(C).

In bodily fluid reception canal Ca, the transfer and distribution of bodily fluids to/over the surface of absorber 12*a* are performed mainly through notch 35*a*, slits 39*a* and slits 39*a*'. However, since hydrophilic sheet 18*j*' configuring connection sheet 18*j* is a liquid permeable non-woven fabric, part of the transfer and distribution may also be performed through such fine pores.

When urine is excreted at the time of wearing absorbent article 104, the total amount of the excreted urine is received in bodily fluid reception canal Ca. The received urine is distributed and discharged from notch 35*a*, slits 39*a* and slits 39*a*' and also from fine pores in hydrophilic sheet 18*j* onto the surface of absorber 12*a*, as it transfers to the front and to the rear within bodily fluid reception canal Ca.

Since connection structure 14*j* has hydrophobic sheet 18*j*" at parts in front of and behind crotch part C, which correspond to the bottom surface of bodily fluid reception canal Ca, and since it therefore does not have an exit for bodily fluids, as a result thereof, urine is not directly discharged onto the part of the absorbent which is present in the crotch part and thus, leakage of urine from the side surfaces of the crotch part is almost certainly prevented.

On the other hand, the amount of urine supplied to the parts present in the front part and the rear part of absorber 12*a* is significantly increased as compared to that in absorbent article 102 shown in FIG. 13.

When feces are excreted at the time of wearing absorbent article 104, the total amount of the excreted feces is received in bodily fluid reception canal Ca. The liquid components within the feces is discharged from slits 39*a* and slits 39*a*' in connection sheet 18*j* and fine pores in hydrophilic sheet 18*j*', similar to urine, whereby the condensed solid components stay within bodily fluid reception canal Ca as is, and thus, urine-feces separation is naturally performed. The feces transfer, depending on the amount thereof, in the direction of the front part within bodily fluid reception canal Ca and thus, spreading to the exterior of bodily fluid reception canal Ca is prevented.

As a general rule, when feces are excreted, changing of the diaper is performed. However, out of all of the wearer's skin, the region that becomes dirty due to the feces is limited to the periphery of the anus, and thus, bed-bath operations by care-takers can be performed more easily. In addition, for the reason stated above, the removal of diapers also becomes easy and thus, the time and effort needed for disposal are reduced.

FIG. 18 contains schematic diagrams illustrating a further embodiment of the absorbent article according to the present invention. FIG. 18(A) is a developed plan view which schematically shows the state in which stress is applied to an absorbent article, in the form of a tape-type diaper for infants, such that it is pulled in the front-rear direction and the lateral direction so as to be developed into a substantially planar form. FIG. 18(B) is a lateral end view along line XVIIIB-XVIIIB in FIG. 18(A) in the above-described state.

Absorbent article 105 shown in FIG. 18 is basically similar to absorbent article 100 shown in FIG. 1; however, the configuration of connection sheet 18*k* in connection structure 14*k* and the form of coupling to top sheet 32 are different.

Connection structure 14*k* used in absorbent article 105 includes a pair of right and left belt-like supporters 16*k* and connection sheet 18*k*, the right and left edge parts thereof respectively coupling to the pair of right and left belt-like supporters 16k at coupling parts 24i. A front end and a rear end of connection structure 14k are respectively coupled to the body of absorbent article 105 with front end coupling part 20d and rear end coupling part 22d.

Belt-like supporters 16k are similar to belt-like supporters 16.

Connection sheet 18k is configured by a hydrophobic spunbond non-woven fabric (made of PE/PET and having a basis weight of 15 g/m$^2$) and includes two notches 35b and 35b' in front body F and in the area ranging from crotch part C to rear body R. Notch 35b present in front body F has a substantially rectangular shape with the length thereof in the front-rear direction being shorter than the width thereof in the lateral direction. Notch 35b' present in the area ranging from crotch part C to rear body R has a substantially rectangular shape with the length thereof in the front-rear direction being longer than the width thereof in the lateral direction.

Connection sheet 18k is coupled to top sheet 32 at coupling parts 26d, 26e, 26f and 26g. Both coupling parts 26d, which are present on both the right and left sides of front body F, extend, in a linear manner, in the front-rear direction. Both coupling parts 26e, which are present on both the right and left sides of rear body R, extend, in a linear manner, in the front-rear direction. Coupling part 26f, which is present in the center in the lateral direction in the area ranging from front body F to crotch part C, extends in belt-like form in the front-rear direction. The width of coupling part 26f is large and thus, such coupling part provides an effect whereby coupling is strengthened and stability is provided by preventing deformation of connection sheet 18k in the periphery of notch 35b. Linear coupling parts 26g are also respectively provided: at the edge on the front side of notch 35b', which is present in the area ranging from crotch part C to rear body R; and in the vicinities of substantially the front side halves of the right and left edges thereof.

In absorbent article 105, the state of coupling of connection sheet 18k to top sheet 32 is similar to that shown in FIG. 6(I), and thus, the shape of bodily fluid reception canal Ca differs depending on the region thereof. More specifically, bodily fluid reception canal Ca assumes a V-shape in crotch part C where it is coupled with belt-like coupling part 26f, while it assumes a U-shape, such as that shown in FIG. 6(J) or FIG. 6(L), in the peripheral areas of notch 35b and 35b' having coupling parts 26d and 26e on the right and left sides thereof.

When urine is excreted at the time of wearing absorbent article 105, the total amount of the excreted urine is received in bodily fluid reception canal Ca. The received urine is distributed and discharged from notches 35b and 35b' onto the surface of absorber 12, as it transfers to the front and to the rear within bodily fluid reception canal Ca.

FIG. 19 contains schematic diagrams illustrating a further embodiment of the absorbent article according to the present invention. FIG. 19(A) is a developed plan view which schematically shows the state in which stress is applied to an absorbent article, in the form of a tape-type diaper for infants, such that it is pulled in the front-rear direction and the lateral direction so as to be developed into a substantially planar form. FIG. 19(B) is a lateral end view along line XIXB-XIXB in FIG. 19(A) in the above-described state.

Absorbent article 106 shown in FIG. 19 is basically similar to absorbent article 100 shown in FIG. 1; however, the configuration of connection sheet 18l in connection structure 14l and the form of coupling to top sheet 32 are different.

Connection structure 14l used in absorbent article 106 includes a pair of right and left belt-like supporters 16l and connection sheet 18l, the right and left edge parts thereof respectively coupling to the pair of right and left belt-like supporters 16l at coupling parts 24j. A front end and a rear end of connection structure 14l are respectively coupled to the body of absorbent article 106 with front end coupling part 20e and rear end coupling part 22e.

Belt-like supporters 16l are similar to belt-like supporters 16.

Connection sheet 18l is configured by the same hydrophobic non-woven fabric as connection sheet 18k, and includes two slits 39b extending in the lateral direction in front body F and four slits 39b' extending in the lateral direction in the area ranging from crotch part C to rear body R.

Connection sheet 18l couples to top sheet 32 at coupling parts 26h and 26i. Coupling part 26h, which is present in the center of crotch part C in the lateral direction, extends in the front-rear direction in belt form, and since the width thereof is large, the coupling is strengthened. Coupling parts 26i, which are presented proximate to slits 39b and 39b' and which respectively extend in the lateral direction, are all provided so that slits 39b and 39b' can be easily opened. In this way, the transfer and distribution of bodily fluids from bodily fluid reception canal Ca onto absorber 12 are performed smoothly.

When urine is excreted at the time of wearing absorbent article 106, the total amount of the excreted urine is received in bodily fluid reception canal Ca. The received urine is distributed and discharged from slits 39b and 39b' onto the surface of absorber 12, as it transfers to the front and to the rear within bodily fluid reception canal Ca. In addition, among slits 39b, a foremost slit that has the largest width in the lateral direction forms an entrance of a front part pocket, which is formed by top sheet 32 and connection structure 14l being sealed off by front end coupling part 20e, and promotes absorption at the front end part of absorber 12, and also prevents an overflow of urine from the front end part thereof. Among slits 39b', a rearmost slit that has the largest width in the lateral direction forms an entrance of a rear part pocket, which is formed by top sheet 32 and connection structure 14l being sealed off by rear end coupling part 22e, and promotes absorption at the rear end part of absorber 12, and also prevents an overflow of urine and feces from the rear end part thereof.

As described above, in one of the preferred embodiments, the connection structure couples to the absorbent article body at the front end and at parts of the right and left edges connecting from the front end thereof, and thus, a front part pocket is formed by such connection structure and such absorbent article body. In addition, in one of the preferred embodiments, the connection structure couples to the absorbent article body at the rear end and at parts of the right and left edges connecting from the rear end thereof, and thus, a rear part pocket is formed by such connection structure and such absorbent article body.

Bodily fluid reception canal Ca in absorbent article 106 assumes, at crotch part C, a deep V-shape that is similar to that shown in FIG. 6(B).

FIG. 20 contains schematic diagrams illustrating a further embodiment of the absorbent article according to the present invention. FIG. 20(A) is a developed plan view which schematically shows the state in which stress is applied to an absorbent article, in the form of a tape-type diaper for infants, such that it is pulled in the front-rear direction and the lateral direction so as to be developed into a substantially planar form. FIG. 20(B) is a lateral end view along line XXB-XXB in FIG. 20(A) in the above-described state.

Absorbent article 107 shown in FIG. 20 is basically similar to absorbent article 100 shown in FIG. 1; however, the configuration of connection sheet 18m in connection structure 14m and the form of coupling to top sheet 32 are different.

Connection structure 14m used in absorbent article 107 includes a pair of right and left belt-like supporters 16m and connection sheet 18m, the right and left edge parts thereof respectively coupling to the pair of right and left belt-like supporters 16m at coupling parts 24k. A front end and a rear end of connection structure 14m are respectively coupled to the body of absorbent article 107 with front end coupling part 20f and rear end coupling part 22f.

Belt-like supporters 16m are similar to belt-like supporters 16.

Connection sheet 18m is configured by the same hydrophobic non-woven fabric as connection sheet 18k, and includes: multiple fine slits 39c extending in the front-rear direction in front body F; lateral C-shaped slits 39c', each extending in the lateral direction at the front end and the rear end of such fine slits 39c; multiple fine slits 39d extending in the front-rear direction in the area ranging from crotch part C to rear body R; and lateral C-shaped slits 39d', each extending in the lateral direction at the front end and the rear end of such fine slits 39d.

Connection sheet 18m couples to top sheet 32 at coupling parts 26j, 26k and 26l. Coupling part 26j, which is present in the center of crotch part C in the lateral direction, extends in the front-rear direction in belt form, and since the width thereof is large, the coupling is strengthened. Coupling parts 26k and 26l, which respectively extend at the center in the lateral direction of the positions of slits 39c and 39d, are both provided so that slit 39c' and 39d' can be easily opened. In this way, the transfer and distribution of bodily fluids from bodily fluid reception canal Ca onto absorber 12 are performed smoothly.

When urine is excreted at the time of wearing absorbent article 107, the total amount of the excreted urine is received in bodily fluid reception canal Ca. The received urine is distributed and discharged from slits 39c, 39c', 39d and 39d' onto the surface of absorber 12, as it transfers to the front and to the rear within bodily fluid reception canal Ca. In addition, among slits 39c', a foremost slit that has the largest width in the lateral direction forms an entrance of a front part pocket, which is formed by top sheet 32 and connection structure 14m being sealed off by front end coupling part 20f, and promotes absorption at the front end part of absorber 12, and also prevents an overflow of urine from the front end part thereof. Among slits 39d', a rearmost slit that has the largest width in the lateral direction forms an entrance of a rear part pocket, which is formed by top sheet 32 and connection structure 14m being sealed off by rear end coupling part 22f, and promotes absorption at the rear end part of absorber 12, and also prevents an overflow of urine and feces from the rear end part thereof.

Bodily fluid reception canal Ca in absorbent article 107 assumes, in the area ranging from crotch part C to rear body R, a deep V-shape that is similar to that shown in FIG. 6(B) and assumes, in part of the area ranging from front body F to crotch part C, a shallow shape in which the canal floats from the surface of the absorber, similar to that shown in FIG. 6(E).

As described above, the absorbent article according to the present invention is illustrated based on the respective embodiments illustrated herein; however, it should be noted that the present invention is not limited to these embodiments and, for example, the configurations of the respective parts may be replaced with any configuration capable of performing a similar function.

In addition, the configurations of the respective parts in the respective embodiments may be combined in an arbitrary manner to obtain other embodiments.

The absorbent article according to the present invention may be preferably used for disposable diapers (for infants and adults), incontinence articles, training pants, or the like.

EXAMPLES

Hereinafter, the present invention will be specifically described by illustrating examples. However, the present invention is not limited thereto.

Wearing tests were conducted as described below, using an absorbent article according to the present invention and a commercially available absorbent article.

1. Absorbent Articles

The absorbent article according to the present invention shown in FIG. 13 was used as Example 1, the absorbent article according to the present invention shown in FIG. 16 was used as Example 2, and the commercially available absorbent article ("Atento," a super-slim underpants-type diaper (size LL) manufactured by Daio Paper Corporation) shown in FIG. 17 was used as Comparison Example 1.

It should be noted that, as described above, both absorbent articles according to the present invention shown in FIGS. 13 and 16 correspond to the absorbent article shown in FIG. 17 having a connection structure incorporated therein. Thus, since the specifications of the diaper bodies are exactly the same, the designed absorption limit amount of the absorber is the same as that for the absorbent article shown in FIG. 17, which is 680 g.

2. Experiment Method

Wearing tests were conducted, using three of each of the absorbent articles of Examples 1 and 2 and Comparison Example 1, with a healthy, 65-year old male repeating wearing and urination. In particular, a test including three cycles of the following (1) to (3) was conducted.

(1) First Cycle (i) Checking of the State at the Time of Wearing

An unused (dry) absorbent article was worn; the position of existence of the penis, the position of existence of the SLGs, and the position of existence of the belt-like supporters (for the Examples) were checked.

(ii) Checking of the State During Motion

After (i), walking, opening and closing of legs, bending and stretching, sitting in a seated position, lateral turning and the like were repeated for approximately 30 minutes, and then misalignment or displacement during motion was checked.

(iii) First Urination Test

When a first urination was performed, the absorbent article was removed and the state of leakage and estimation of a leakage amount were checked.

When leakage occurred, the wearing test was terminated. After weighing the absorbent article as is and measuring the absorption amount, the waist seal was cut in order to analyze: the state of absorption and the state of leakage thereof; and the state of absorption and the state of deformation of the crotch region.

When leakage did not occur, after weighing the absorbent article as is and measuring the absorption amount, such absorbent article was worn again and the wearing test was continued.

(2) Second Cycle (i) Checking of the State at the Time of Wearing

The moistened absorbent article after the first urination test was worn; the position of existence of the penis, the position of existence of the SLGs, and the position of existence of the belt-like supporters (for the Examples) were checked.

(ii) Checking of the State During Motion

After (i), walking, opening and closing of legs, bending and stretching, sitting in a seated position, lateral turning and the like were repeated for approximately 30 minutes, and then misalignment or displacement during motion was checked.

(iii) Second Urination Test

When a second urination was performed, the absorbent article was removed and the state of leakage and estimation of a leakage amount were checked.

When leakage occurred, the wearing test was terminated. After weighing the absorbent article as is and measuring the absorption amount, the waist seal was cut in order to analyze: the state of absorption and the state of leakage thereof; and the state of absorption and the state of deformation of the crotch region.

When leakage did not occur, after weighing the absorbent article as is and measuring the absorption amount, such absorbent article was worn again and the wearing test was continued.

(3) Third Cycle (i) Checking of the State at the Time of Wearing

The moistened absorbent article after the second urination test was worn; the position of existence of the penis, the position of existence of the SLGs, and the position of existence of the belt-like supporters (for the Examples) were checked.

(ii) Checking of the State During Motion

After (i), walking, opening and closing of legs, bending and stretching, sitting in a seated position, lateral turning and the like were repeated for approximately 30 minutes, and then misalignment or displacement during motion was checked.

(iii) Third Urination Test

When a third urination was performed, the absorbent article was removed and the state of leakage and estimation of a leakage amount were checked.

After weighing the absorbent article as is and measuring the absorption amount, the waist seal was cut in order to analyze: the state of absorption and the state of leakage thereof; and the state of absorption and the state of deformation of the crotch region.

It should be noted that the above-described respective urination tests were conducted in two types of body positions, i.e. the prone position and the supine position.

The prone position is a body position in which urine tends to concentrate in the absorber present in the front part, and thus, the absorber present in the rear part is not effectively utilized. Accordingly, the challenge is how to make use of the absorber present in the rear part without applying absorption load to the crotch part.

The supine position is a body position in which urine tends to concentrate in the absorber present in the rear part, and thus, the absorber present in the front part is not effectively utilized. Accordingly, the challenge is how to make use of the absorber present in the front part without applying absorption load to the crotch part.

3. Result

The result is shown in Tables 1-3. It should be noted that Table 1 describes average values of the three absorbent articles.

Figure 21:
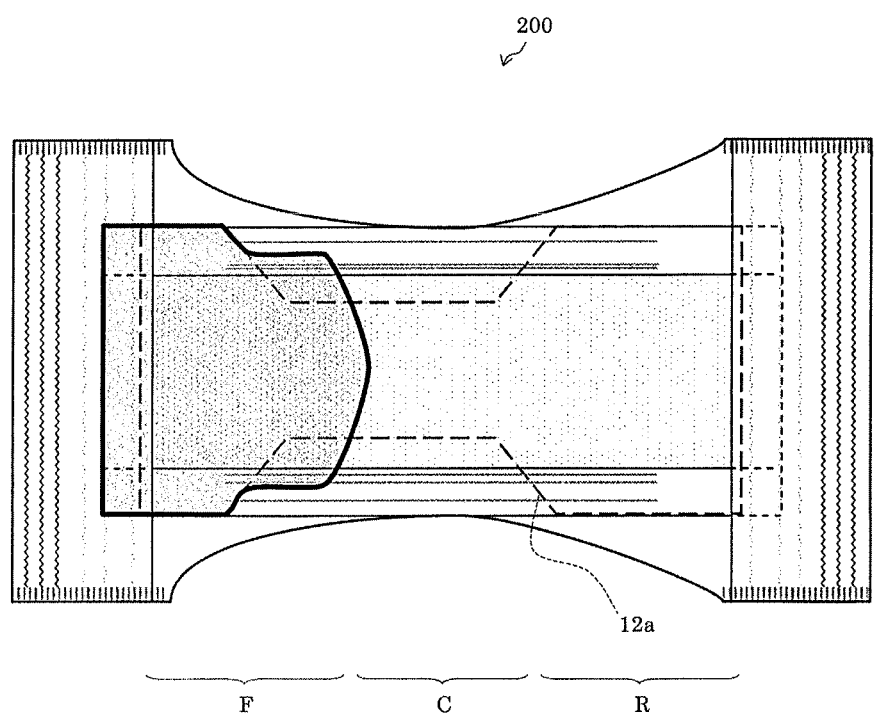
FIG. 21 is a schematic plan view illustrating the state of absorption of urine after first urination in the prone position of Comparison Example 1.
Figure 22:
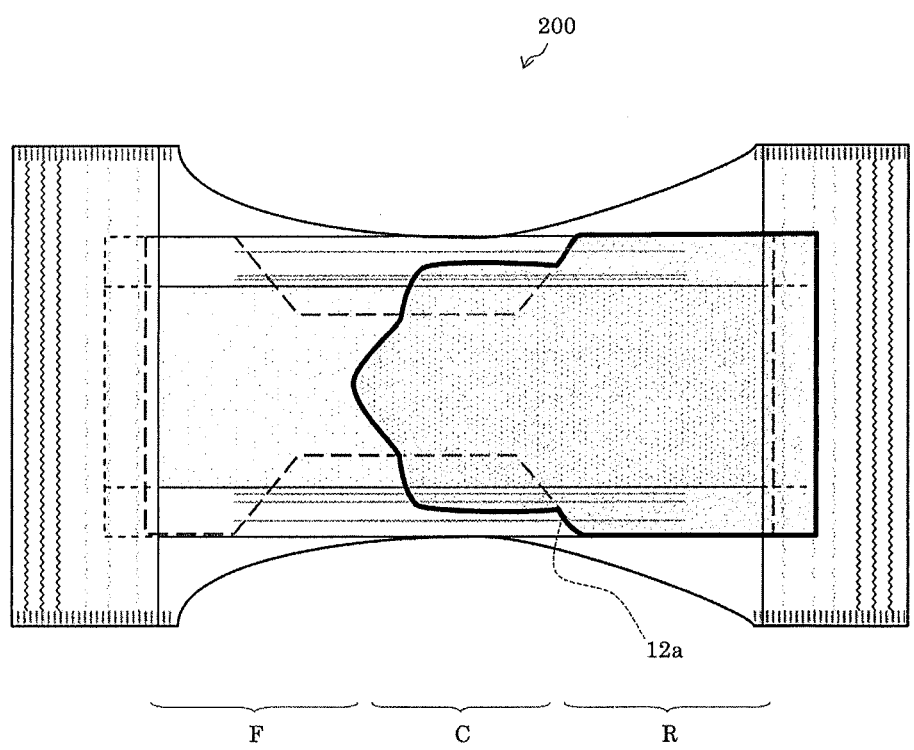
FIG. 22 is a schematic plan view illustrating the state of absorption of urine after first urination in the supine position of Comparison Example 1.
Figure 23:
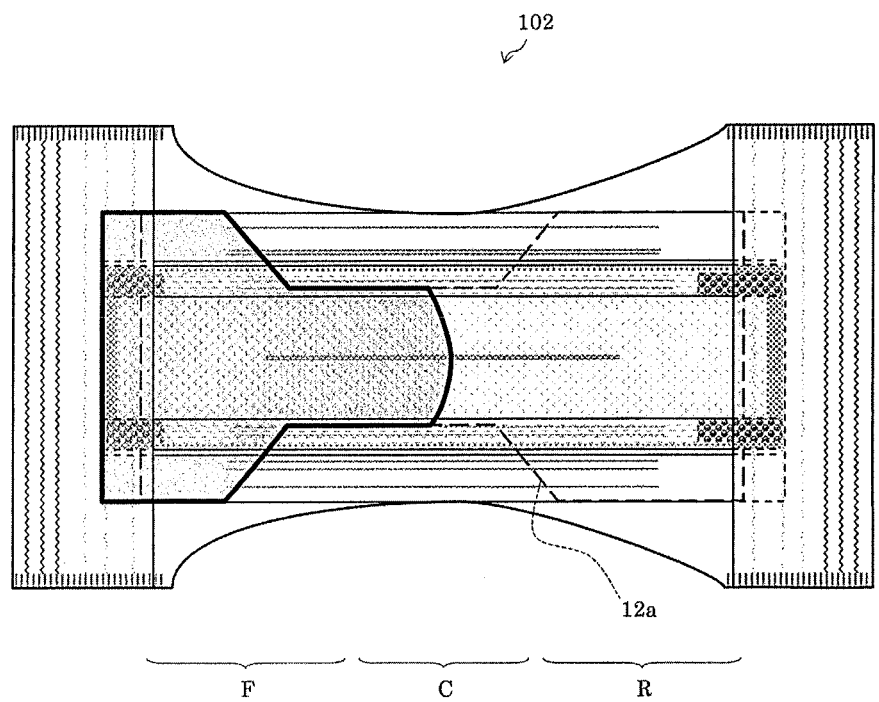
FIG. 23 is a schematic plan view illustrating the state of absorption of urine after first urination in the prone position of Example 1.
Figure 24:
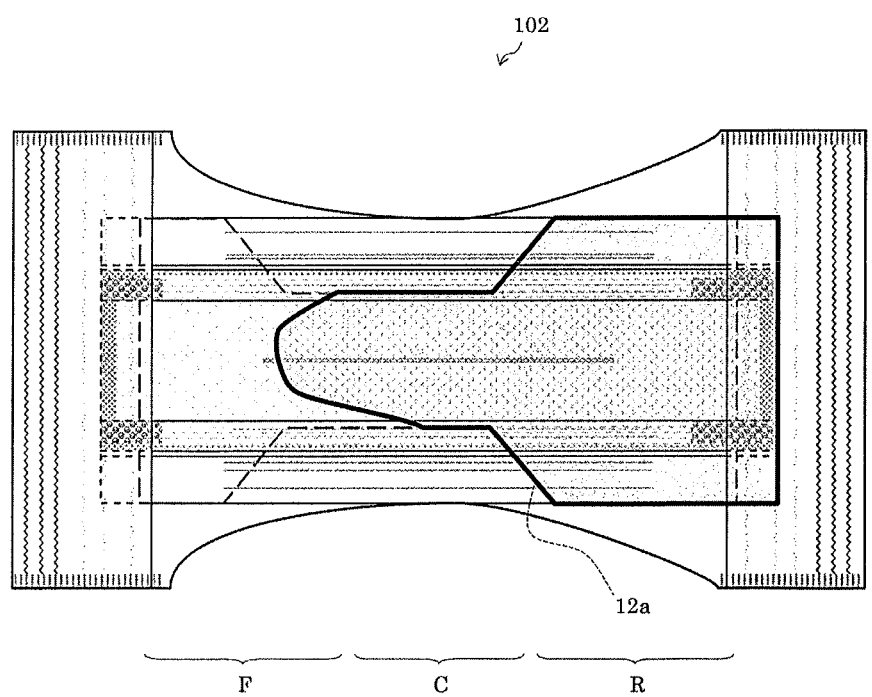
FIG. 24 is a schematic plan view illustrating the state of absorption of urine after first urination in the supine position of Example 1.
Figure 25:
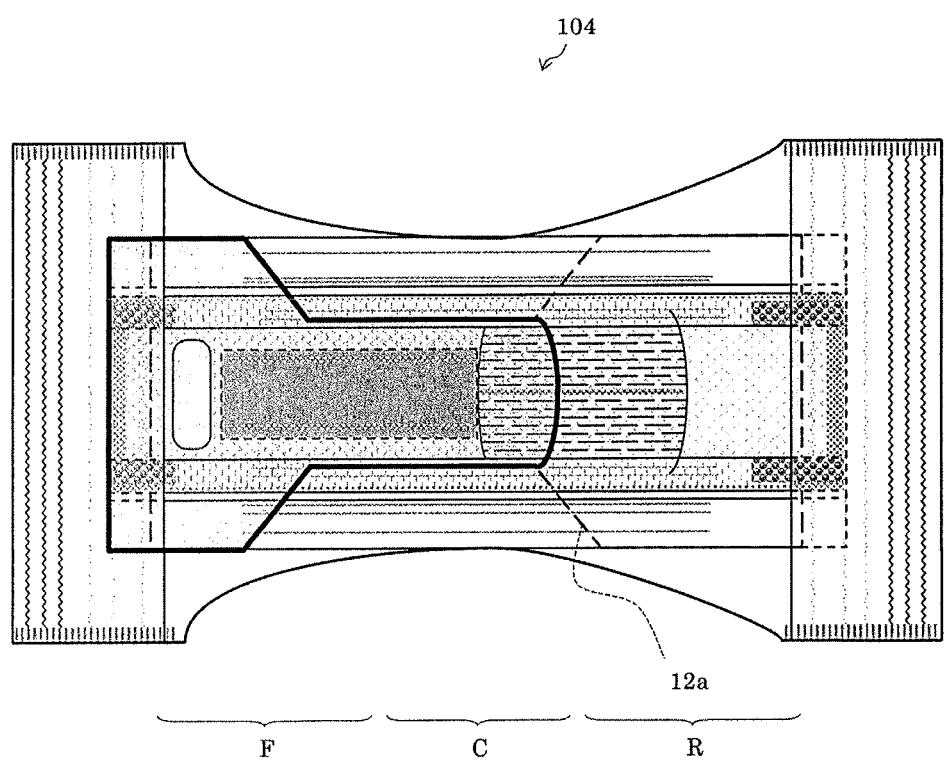
FIG. 25 is a schematic plan view illustrating the state of absorption of urine after first urination in the prone position of Example 2
Figure 26:
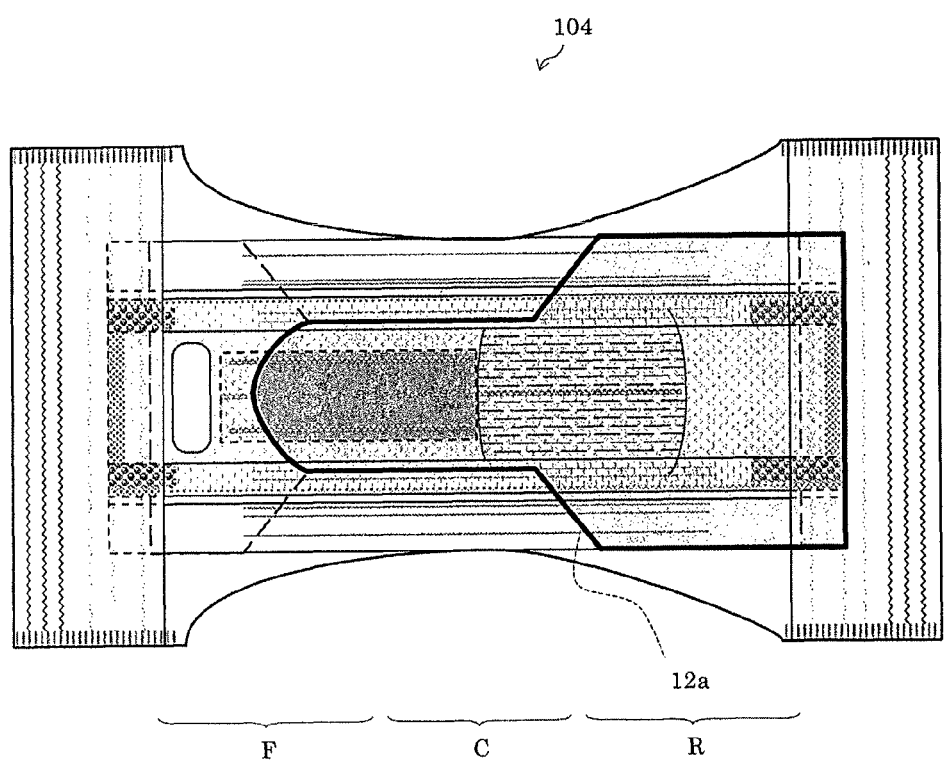
FIG. 26 is a schematic plan view illustrating the state of absorption of urine after first urination in the supine position of Example 2.
Figure 27:
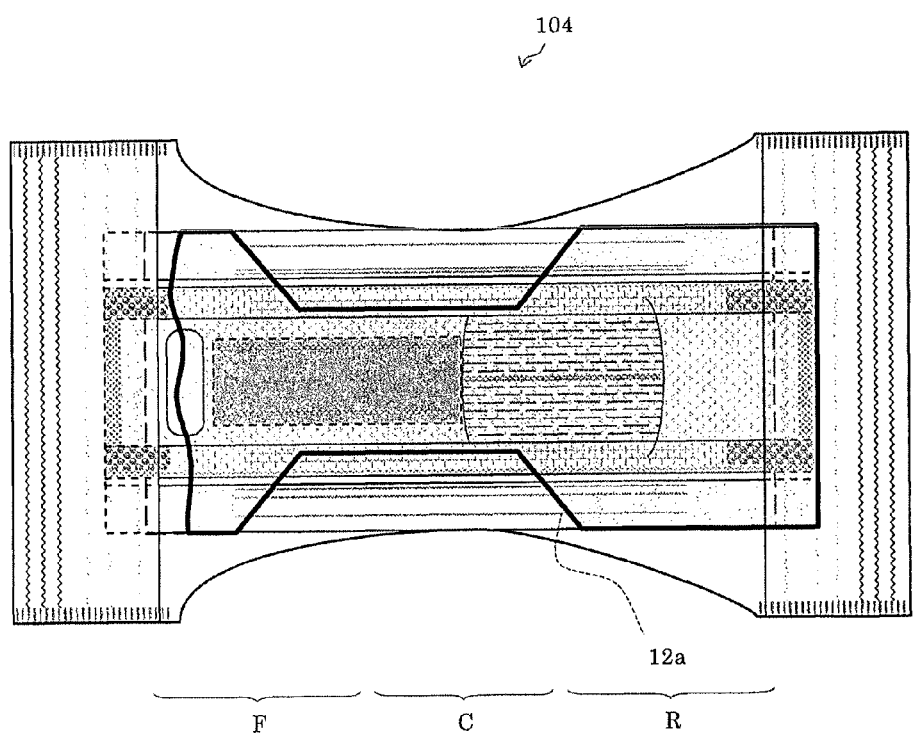
FIG. 27 is a schematic plan view illustrating the state of absorption of urine after second urination in the supine position of Example 2.
Figure 28:
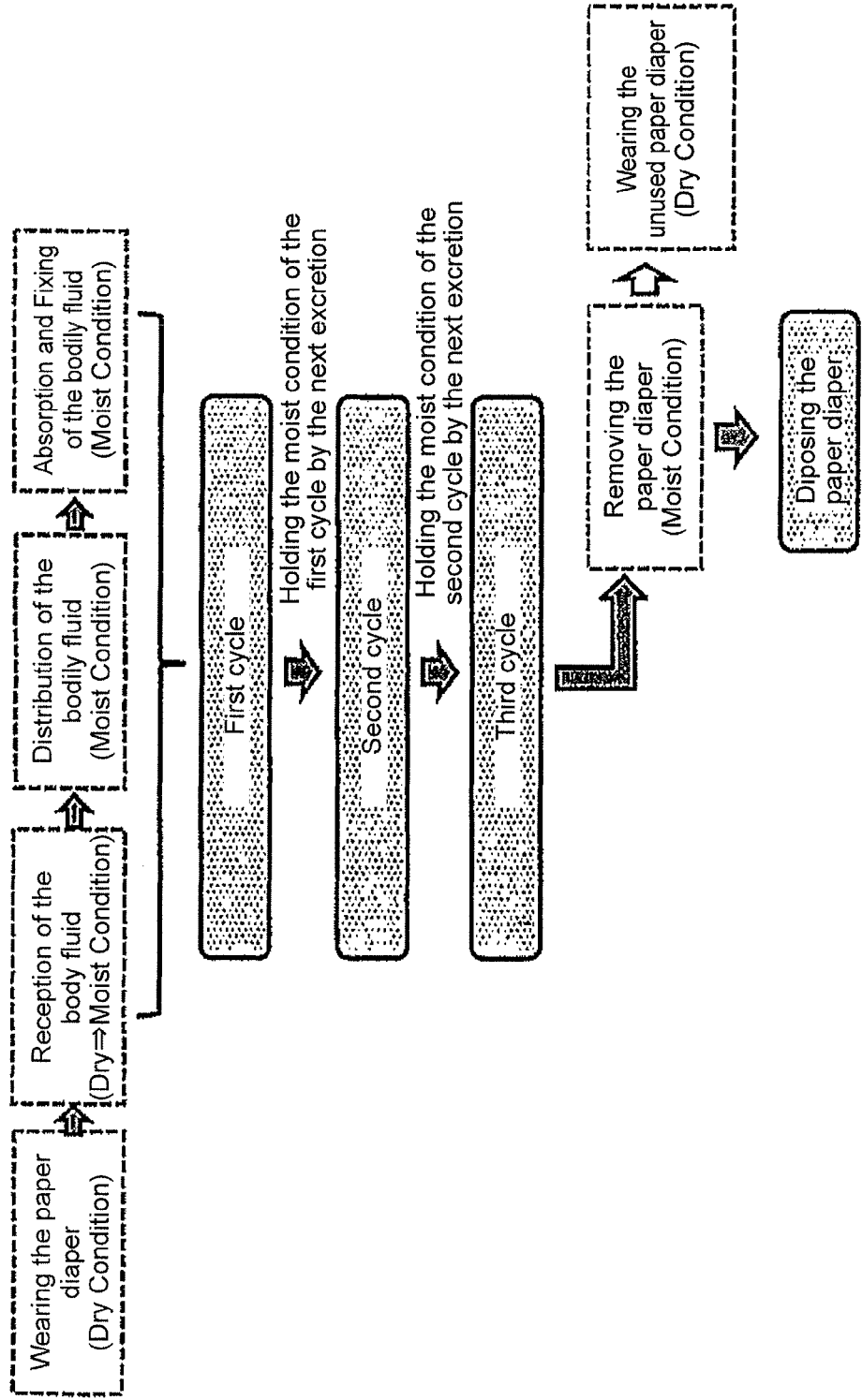
FIG. 28 is a diagram illustrating a life cycle of a disposable diaper.

In addition, FIGS. 21 to 27 show approximate states of absorption of urine. The area surrounded by the bold frame border in the respective drawings represents the area where the absorption of urine was confirmed. FIG. 21 is a schematic plan view illustrating the state of absorption of urine after first urination in the prone position of Comparison Example 1. FIG. 22 is a schematic plan view illustrating the state of absorption of urine after first urination in the supine position of Comparison Example 1. FIG. 23 is a schematic plan view illustrating the state of absorption of urine after first urination in the prone position of Example 1. FIG. 24 is a schematic plan view illustrating the state of absorption of urine after first urination in the supine position of Example 1. FIG. 25 is a schematic plan view illustrating the state of absorption of urine after first urination in the prone position of Example 2. FIG. 26 is a schematic plan view illustrating the state of absorption of urine after first urination in the supine position of Example 2. FIG. 27 is a schematic plan view illustrating the state of absorption of urine after second urination in the supine position of Example 2.

TABLE 1

Table 1: Urine Absorption Performance and Leakage Occurrence

| | | Absorbent | | |
|---|---|---|---|---|
| | Article Considerations | Example 1 (see FIG. 13) | Example 2 (see FIG. 16) | Comparative Example 1 (see FIG. 17) |
| | Designed limit amount for urine absorption amount | 680 g | 680 g | 680 g |
| Prone position | $1^{st}$ cycle absorption amount | 250 g | 300 g | 140 g |
| | $1^{st}$ cycle leakage amount | Approx. 20 g | None | Approx. 40 g |
| | $2^{nd}$ cycle absorption amount | — | 230 g | — |
| | $2^{nd}$ cycle leakage amount | — | Approx. 15 g | — |
| | Total absorption amount | 250 g | 530 g | 140 g |
| | Absorption efficiency (wrt limit absorption amount) | 37% | 78% | 21% |

TABLE 1-continued

Table 1: Urine Absorption Performance and Leakage Occurrence

| Article Considerations | | Absorbent | | |
|---|---|---|---|---|
| | | Example 1 (see FIG. 13) | Example 2 (see FIG. 16) | Comparative Example 1 (see FIG. 17) |
| Supine position | $1^{st}$ cycle absorption amount | 342 g | 330 g | 320 g |
| | $1^{st}$ cycle leakage amount | None | None | Approx. 30 g |
| | $2^{nd}$ cycle absorption amount | 220 g | 240 g | — |
| | $2^{nd}$ cycle leakage amount | Approx. 10 g | None | — |
| | $3^{rd}$ cycle absorption amount | — | 160 g | — |
| | $3^{rd}$ cycle leakage amount | — | Approx. 50 g | — |
| | Total absorption amount | 562 g | 730 g | 320 g |
| | Absorption efficiency (wrt limit absorption amount) | 83% | 107% | 47% |

TABLE 2

Table 2: Observations of Crotch Part Absorption/Deformation

| Article Considerations | Absorbent | | |
|---|---|---|---|
| | Example 1 (see FIG. 13) | Example 2 (see FIG. 16) | Comparative Example 1 (see FIG. 17) |
| Utilization of absorbent present in crotch part | The entire absorbent absorbed urine uniformly; however, it was not yet swollen and was still flat and thus, there was room for further absorption Top sheet in contact with R/L SLGs was still dry | The entire absorbent absorbed urine uniformly; however, it was not yet swollen and was still flat and thus, there was room for further absorption Top sheet in contact with R/L SLGs was still dry | SAP sufficiently swelled and the entire absorbent was utilized Top sheet was wet up to the vicinities of R/L SLGs |
| Occurrence of side leakage from crotch part | No side leakage from crotch part was observed until the end of the $2^{nd}$ cycle Even when leakage from front part and rear part started, side leakage did not occur | No side leakage from crotch part was observed until the end of the $3^{rd}$ cycle Even when leakage from front part and rear part started, side leakage did not occur | Entire upper surface of left SLG was wet Leakage occurred from left side surface Part of upper surface of right SLG was wet Oozing occurred from right side surface |
| Deformation of crotch part | Substantially no deformation was seen as compared to the time of wearing | Substantially no deformation was seen as compared to the time of wearing | Deformation due to compression as if pushed into a small space |

TABLE 3

Table 3: Wearing Performance

| Article Considerations | | Absorbent | | |
|---|---|---|---|---|
| | | Example 1 (see FIG. 13) | Example 2 (see FIG. 16) | Comparative Example 1 (see FIG. 17) |
| Position of penis and change thereof at the time of wearing (as one indicator for position misalignment) | $1^{st}$ cycle When worn (dry) | 12-13 cm above upper end of absorber Held straight in the vicinity of center part | 12-13 cm above upper end of absorber Held straight in the vicinity of center part | 11-12 cm above upper end of absorber Bent a little to the lower right |
| | $1^{st}$ cycle During motion (dry) | No significant difference was observed from when worn | No significant difference was observed from when worn | Shifted a little to the front and rear and to both sides in accordance with motion |
| | $1^{st}$ cycle After urination (moist) | No significant difference was observed from when worn | No significant difference was observed from when worn | 10-11 cm above upper end of absorber Bent a lot to the lower right |
| | $2^{nd}$ cycle When worn (moist) | 12-13 cm above upper end of absorber Held straight in the vicinity of center part | 12-13 cm above upper end of absorber Held straight in the vicinity of center part | Test terminated due to occurrence of leakage |
| | $2^{nd}$ cycle After urination (moist) | No significant difference was observed from when worn | No significant difference was observed from when worn | Test terminated due to occurrence of leakage |

TABLE 3-continued

Table 3: Wearing Performance

| Article Considerations | | Absorbent | | |
|---|---|---|---|---|
| | | Example 1 (see FIG. 13) | Example 2 (see FIG. 16) | Comparative Example 1 (see FIG. 17) |
| Occurrence of hot and stuffy state and skin-wetting at the time of wearing | $1^{st}$ cycle From the time of wearing to urination (dry) and removal | Slight feeling of hot and stuffy state and being compressed No sign of skin-wetting when removed | Slight feeling of hot and stuffy state and being compressed No sign of skin-wetting when removed | Felt stuffy due to compression Skin parts in contact with absorber when removed were soaking wet |
| | $2^{nd}$ cycle From the time of wearing to urination (moist) | Slight feeling of hot and stuffy state and being compressed No sign of skin-wetting when removed | Slight feeling of hot and stuffy state and being compressed No sign of skin-wetting when removed | Test terminated due to occurrence of leakage |

(1) State of Absorption in Prone Position (Table 1)

As shown in Table 1, regarding the absorbent articles of Comparison Example 1 and Example 1, leakage occurred in all three absorbent articles in the first cycle (first urination); however, it can be seen that Example 1 has a higher amount of absorption than that of Comparison Example 1, and that, thus, the absorption efficient is nearly double. As is clear from the comparison between FIG. 21 and FIG. 23, this is considered to be because, in Example 1, the absorption area extends more in the rear body direction as compared to Comparison Example 1 and because, in Comparison Example 1, the state of absorption of crotch part C is such that urine reaches to the top of the SLGs and thus, side leakage occurs early, whereas in Example 1, urine stays at the part of the absorber and does not transfer to the inner sides of the SLGs.

In addition, regarding the absorbent article of Example 2, no leakage occurred in all three absorbent articles in the first cycle (first urination); however, in the second cycle (second urination), leakage occurred in two out of three absorbent articles; and thus, they were not provided in the third cycle. In Example 2, the total amount of absorption of the first urination and the second urination is nearly four times that of Comparison Example 1, and thus, the absorption efficiency is increased by up to 78%. As is clear from the comparison among FIGS. 21, 23 and 25, this is considered to be because, after the first cycle (first urination), the absorption area is further extended to the rear body direction as compared to Comparison Example 1 and because the state of absorption in crotch part C is such that, similar to Example 1, the urine does not transfer to the roots of the SLGs and stays at the part of the absorber.

In both Examples 1 and 2, the occurrence of leakage was due to an overflow from the front part terminal part and no leakage from the crotch part was observed. This is considered to be because the utilization of the absorber present in the rear part was promoted due to the effect of the transfer and distribution of urine by means of bodily fluid reception canal Ca, which bypasses crotch part C.

(2) State of Absorption in Supine Position (Table 1)

The amount of absorption in the supine position was significantly higher in all of the absorbent articles of both the Examples and the Comparison Example, as compared to that of the amount of absorption in the prone position. This is considered to be because, in the supine position, the absorption area, which is utilized for absorption, is enlarged as compared to the above-described prone position.

As shown in Table 1, regarding the absorbent article of Comparison Example 1, leakage occurred in all three absorbent articles in the first cycle (first urination); however, regarding the absorbent articles of Examples 1 and 2, no leakage occurred in any of the three absorbent articles in the first cycle (first urination). In addition, regarding the absorbent article of Example 2, no leakage occurred in two out of three absorbent articles in the second cycle (second urination) and a small amount of leakage occurred in one absorbent article; however they were still provided in the third cycle. Leakage occurred in all three absorbent articles in the third cycle (third urination).

Regarding the total amount of absorption, such amount in Example 1 was approximately 1.8 times that of Comparison Example 1, and such amount in Example 2 was approximately 2.3 times that of Comparison Example 1. The absorption efficiency was 47% for Comparison Example 1, whereas, it was 83% for Example 1 and 107% for Example 2, which exceeded the designed limit amount. It is considered that the reason why it was able to absorb such an amount of urine, which exceeded the designed limit amount, is because part of the absorber (SAP) was utilized without receiving pressure. As is clear from the comparison among FIGS. 22, 24, 26 and 27, this is considered to be because: in Examples 1 and 2, after the first cycle (first urination), the absorption area extends more in the rear body direction as compared to Comparison Example 1; in particular, in Example 2, after the second cycle (second urination), the absorption area extends up to the vicinity of the front end of absorber 12; and the state of absorption of crotch part C is such that, while, in Comparison Example 1, urine reaches the top of the SLGs and thus, side leakage occurred early, it does not transfer to the roots of the SLGs and urine stays at the part of the absorber.

In both Examples 1 and 2, the occurrence of leakage was due to an overflow from the rear part terminal part and no leakage from the crotch part was observed. This is considered to be because the utilization of the absorber present in the front part was promoted due to the effect of the transfer and distribution of urine by means of bodily fluid reception canal Ca, which bypasses crotch part C.

(3) Utilization State of Absorber Present in Crotch Part (Table 2)

In the absorbent article of Comparison Example 1, urine is directly excreted to the vicinity of the crotch part and thus, a larger load is applied to the absorber present in the crotch part, whereas in the absorbent articles of Examples 1 and 2, the total amount of urine is accommodated in bodily fluid reception canal Ca and it transfers and is distributed to the front and to the rear, and thus, the urine reached the absorber present in the crotch part due to the spreading in the front-rear direction. For this reason, major differences existed, such as those shown in Table 2.

(4) Occurrence State of Side Leak from Crotch Part (Table 2)

Major differences existed, such as those shown in Table 2, based on the difference in the mechanisms for urine transfer and distribution, which is associated with the presence or absence of above-described bodily fluid reception canal Ca.

(5) Deformation State of Crotch Part (Table 2)

In the absorbent article of Comparison Example 1, since the surface of the wearer's skin makes direct contact with the crotch part, the entire crotch part, which includes the absorbent therein, bends and is deformed by motion, and thus, so-called bunching (bumps) was generated. In contrast, in the absorbent articles of Examples 1 and 2, the surfaces of the belt-like supporters, which are present at the upper ends of the connection structure that forms bodily fluid reception canal Ca, make direct contact with the surface of the wearer's skin. Since there is no chance of the wearer's skin making direct contact with the crotch part, only slight deformation occurred in the crotch part.

(6) Position of Penis and Change Thereof at the Time of Wearing (as One Indicator for Position Misalignment) (Table 3)

In the absorbent article of Comparison Example 1, as shown in Table 3, transferring to the right or to the left and/or bending was/were observed, depending on the difference between the dry state and the moistened state, or the absence or presence of motion, whereas in the absorbent articles of Examples 1 and 2, little positional change occurred regardless of the difference between the dry state and the moistened state, or the absence or presence of motion.

In the absorbent article of Comparison Example 1, the penis was constantly in direct contact with the absorber surface, which was relatively wide in the front, in the rear, and at both sides thereof, over the entire duration of use of the absorbent article, and thus, the position thereof had to change in accordance with the movement of the diaper body. On the other hand, in the absorbent articles of Examples 1 and 2, the entire penis, including the testicular region, ran through the center part of the absorbent article in the front-rear direction, was accommodated inside bodily fluid reception canal Ca, which was spaced-apart from the absorber surface, and was enclosed by soft non-woven fabric, and thus, the penis was kept in a state which was independent of the movement of the absorbent article body.

(7) Occurrence State of Heating and Skin-Wetting at the Time of Wearing (Table 3)

In the absorbent article of Comparison Example 1, since the substantial part of the lower abdominal region and the hips kept on directly contacting the absorber surface, which was relatively wide in the front, in the rear, and at both sides thereof, in a compressive manner over the entire duration of use of the diaper, even in a dry state, such region and hips received friction caused by the movement of the absorbent article body and thus, a feeling of pressure was inevitable. Even in a moistened state, the same state continued and thus, the avoidance of the occurrence of heating and skin-wetting was almost impossible. On the other hand, in the absorbent articles of Examples 1 and 2, the entire penis, including the testicular region, ran through the center part of the absorbent article in the front-rear direction and was accommodated inside bodily fluid reception canal Ca, which was spaced-apart from the absorber surface. Since the substantial part of the lower abdominal region and the hips was isolated by bodily fluid reception canal Ca, compression was unlikely to occur. Since only the tip of the penis became wet at the time of urination, the occurrence of heating was avoided, even after long-term use until the end of the second cycle, as shown in Table 3.

DESCRIPTIONS OF REFERENCE NUMERALS 10,10',10a leak preventer
12,12',12a,13 absorber
14,14',14a,14b,14c,14d,14e,14f,14g,14h,14i,14j,14k,14l, 14m connection structure
16,16',16a,16h,16i,16j,16k,16l,16m,17a,17b,17c,17d,17e, 17f,17g,17h,17i,17j,17k belt-like supporters
17',17a',17f',17g',17h',17i',17j',17k' stretchable members
17",17a",17f",17g",17h",17i",17j",17k" non-woven fabric
18,18'18a,18b,18c,18d,18d',18e,18f,18g,18h,18i,18j,18k, 18l,18m,19,19a,19b,19c,19d,19e,19f,19g,19h,19i,19j, 19k,19l,19m,19n,19o,19p connection sheet
18b',18c',18d',18j'" hydrophobic sheet
18b",18c",18d',18j' hydrophilic sheet
20,20a,20b,20c,20d,20e,20f front end coupling part
22,22a,22b,22c,22d,22e,22f rear end coupling part
24,24a,24b,24c,24d,24e,24f,24g,24h,24i,24j,24k,26,26a, 26b,26c,26d,26e,26f,26g,26h,26i,26j,26k,26l,27,27a,27b, 27b',27c,27c' coupling part
28 Detachable members
30 outer leg gathers (OLG)
32, 32a top sheet
34,34a,34b,34c,34d,35,35a,35b,35b' notch
36,36a,36b,36c opening
38,38a,38b,38c,38d,38e,38f,39,39',39a,39a',39b,39b',39c, 39c',39d,39d' slit
40 external covering sheet
42 waist gather
44 shirring gather
46 stereoscopic leg gather (SLG)
100,101,102,103,104,105,106,107,200 absorbent article
C crotch part
Ca bodily fluid reception canal
F front body
NA non-stretchable areas
R rear body
SA stretchable areas

The invention claimed is:
1. An absorbent article comprising:
an absorbent article body that has a leak preventer in sheet form and an absorber capable of absorbing a bodily fluid, at least one layer thereof being arranged above the leak preventer; and
a connection structure that is arranged from a front end part to a rear end part of the absorbent article body in the length direction via a front body, a crotch part and a rear body, wherein:
the connection structure has a pair of right and left belt-shaped supporters and a connection sheet, right and left edge parts of the connection sheet respectively coupling to an underside of the pair of right and left belt-shaped supporters;
a right edge part of the right belt-shaped supporter and a left edge part of the left belt-shaped supporter are not coupled to the leak preventer directly, nor through one or more intermediate members, along a longitudinal direction in the crotch part;

the connection sheet hangs down, on an underside of the belt-shaped supporters, toward the absorber in the front body, the crotch part and the rear body;

a bodily fluid reception canal is formed with vicinities of the right and left edge parts of the connection sheet serving as side surfaces and a vicinity of a center part of the connection sheet in the lateral direction serving as a bottom surface;

the bodily fluid reception canal receives a bodily fluid excreted from a wearer and transfers to the absorber;

a part of an under surface of the connection sheet configuring the bottom surface of the bodily fluid reception canal and a surface of the absorber are coupled together;

a part or the entirety of the connection sheet is composed of a non-woven fabric including a hydrophobic non-woven fabric, a hydrophilic non-woven fabric, or a non-woven fabric including both a hydrophobic part and a hydrophilic part;

the connection sheet is provided with pores in the non-woven fabric and at least an opening or a slit that is larger than the pores and configured to form an exit for transferring the bodily fluid excreted from the wearer to the absorber; and a front end part and a rear end part of the connection structure are respectively coupled along a front end and a rear end of the absorbent article body.

2. The absorbent article according to claim 1, wherein a part of the connection sheet configuring the bottom surface has a part that is not coupled to the surface of the absorber in the crotch part.

3. The absorbent article according to claim 1, wherein a part of the connection sheet configuring the bottom surface has a part that is not coupled to the surface of the absorber over the entire width of the bottom surface in the lateral direction, at least at one location in the front-rear direction.

4. The absorbent article according to claim 1, wherein the bodily fluid reception canal has an opening at an upper part thereof.

5. The absorbent article according to claim 1, wherein the belt-shaped supporters have stretchability in at least part thereof.

6. The absorbent article according to claim 1, wherein the connection sheet that configures the bodily fluid reception canal is provided with the notch.

7. The absorbent article according to claim 1, wherein the connection sheet that configures the bodily fluid reception canal is provided with the opening.

8. The absorbent article according to claim 1, wherein the connection sheet that configures the bodily fluid reception canal is provided with the slit.

9. The absorbent article according to claim 1, wherein the part or the entirety of the connection sheet is composed of the hydrophobic non-woven fabric.

10. The absorbent article according to claim 1, wherein the part or the entirety of the connection sheet is composed of the hydrophilic non-woven fabric.

11. The absorbent article according to claim 1, wherein the part or the entirety of the connection sheet is composed of the non-woven fabric including both the hydrophobic part and the hydrophilic part.

12. The absorbent article according to claim 1, wherein the connection structure is coupled to the absorbent article body, at a front end thereof and parts of right and left edges thereof that continue from the front end, and a front part pocket is formed by the connection structure and the absorbent article body.

13. The absorbent article according to claim 1, wherein the connection structure is coupled to the absorbent article body, at a rear end thereof and parts of right and left edges thereof that continue from the rear end, and a rear part pocket is formed by the connection structure and the absorbent article body.

14. The absorbent article according to claim 1, wherein a degree of hanging of the bodily fluid reception canal decreases from the crotch part to the rear body, the degree of hanging (h/w) being a ratio of a distance (h) between a plane connecting upper surfaces of the band-like supporters and a bottom surface of the connection sheet with respect to an inner interval (w) between the pair of right and left belt-shaped supporters.

15. The absorbent article according to claim 1, wherein a degree of hanging of the bodily fluid reception canal decreases from the crotch part to the front body, the degree of hanging (h/w) being a ratio of a distance (h) between a plane connecting upper surfaces of the band-like supporters and a bottom surface of the connection sheet with respect to an inner interval (w) between the pair of right and left belt-shaped supporters.

16. The absorbent article according to claim 1, wherein inner leg gathers are further provided on exterior sides of the bodily fluid reception canal in the lateral direction.

17. The absorbent article according to claim 1, wherein outer leg gathers are further provided on right and left edge parts of the absorbent article body.

18. The absorbent article according to claim 1, wherein the belt-shaped supporters are parallel polyurethane filaments covered by non-woven fabric.

19. The absorbent article according to claim 1, wherein the pair of right and left belt-shaped supporters is only disposed in a central region of a width direction of the absorbent article.

* * * * *